(12) United States Patent
Sugiyama et al.

(10) Patent No.: US 7,402,412 B2
(45) Date of Patent: Jul. 22, 2008

(54) MUTATED D-AMINOTRANSFERASE AND METHOD FOR PRODUCING OPTICALLY ACTIVE GLUTAMIC ACID DERIVATIVES USING THE SAME

(75) Inventors: Masakazu Sugiyama, Kanagawa (JP); Kunihiko Watanabe, Kanagawa (JP); Tatsuki Kashiwagi, Kanagawa (JP); Ei-ichiro Suzuki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 21 days.

(21) Appl. No.: 11/148,410

(22) Filed: Jun. 9, 2005

(65) Prior Publication Data
US 2006/0003411 A1 Jan. 5, 2006

Related U.S. Application Data

(63) Continuation of application No. PCT/JP03/015714, filed on Dec. 9, 2003.

(30) Foreign Application Priority Data

Dec. 9, 2002 (JP) ............... 2002-357043
Jun. 26, 2003 (JP) ............... 2003-183290

(51) Int. Cl.
C12P 13/14 (2006.01)
C12P 21/06 (2006.01)
C12N 1/21 (2006.01)
C07H 21/04 (2006.01)

(52) U.S. Cl. ............ 435/110; 435/69.1; 435/193; 435/320.1; 435/252.3; 435/325; 536/23.2

(58) Field of Classification Search ............ 435/69.1, 435/193, 110; 536/23.1
See application file for complete search history.

(56) References Cited

U.S. PATENT DOCUMENTS 5,994,559 A 11/1999 Abushanab et al.
6,337,190 B1 1/2002 Hwang et al.
6,635,749 B2 * 10/2003 Frankel ............ 536/23.1

FOREIGN PATENT DOCUMENTS

EP 0 736 604 A2 10/1996

WO WO 03/056026 7/2003

OTHER PUBLICATIONS

D. de Jesus Oliveira, et al., "Diastereoselective Formation of A Quaternary Center in A Pyroglutamate Derivative. Formal Synthesis of Monatin", Tetrahedron Letters, vol. 42, pp. 6793-6796, 2001.
K. Nakamura, et al., "Total Synthesis of Monatin", Organic Letters, vol. 2, No. 19, pp. 2967-2970, Jun. 23, 2000.
C.W. Holzapfel, "A Simple Cycloaddition Approach to A Racemate of the Natural Sweetener Monatin", Synthetic Communication, vol. 24, No. 22, pp. 3197-3211, 1994.
C.W. Holzapfel, "The Synthesis of A Gamma-Keto-Alpha-Amino Acid, A Key Intermediate in the Synthesis of Montain, A New Natural Sweetener", Synthetic Communications, vol. 23, No. 18, pp. 2511-2526, 1993.
Database UniProt [Online] "D-Alanine Aminotransferase (EC 2.6.1.21) (D-Aspartate Aminotransferase) (D-Amino Acid Aminotransferase) (D-Amino Acid Transaminase) (DAAT)", XP-002383319, Database accession no. DAAA_BACSH, Oct. 1, 1996.
P.W. Van Ophem, et al., "Catalytic Ability and Stability of Two Recombinant Mutants of D-Amino Acid Transaminase Involved in Coenzyme Binding", Protein Science, 4, 1995, pp. 2578-2586, XP-002383317.
I.G. Fotheringham, et al., "Characterization of the Genes Encoding D-Amino Acid Transaminase and Glutamate Racemase, Two D-Glutamate Biosynthetic Enzymes of Bacillus sphaericus ATCC 10208", Journal of Bacteriology, vol. 180, No. 16, pp. 4319-4323, Aug. 1998.
S. Sugio, et al., "Crystal Structure of a D-Amino Acid Aminotransferase: How the Protein Controls Stereoselectivity", Biochemistry, vol. 34, No. 30, pp. 9661-9669, 1995.
H.-S. RO, et al., "Site-Directed Mutagenesis of the Amino Acid Residues in Beta-Strand III (VAL30-VAL36) of D-Amino Acid Aminotransferase OB Bacillus SP. YM-1", FEBS Letters, vol. 398, No. 2-3, pp. 141-145, Dec. 2, 1996.
K. Kishimoto, et al., "Role of Leucine 201 of Themostable D-Amino Acid Aminotransferase from A Thermophile, Bacillus SP. YM-1", J. Biochem., vol. 117, No. 4, pp. 691-696, Apr. 1995.

* cited by examiner

Primary Examiner—Rebecca E. Prouty
Assistant Examiner—Md. Younus Meah
(74) Attorney, Agent, or Firm—Oblon, Spivak, McClelland, Maier & Neustadt, P.C.

(57) ABSTRACT

A D-aminotransferase can be modified so as to efficiently produce (2R, 4R)-monatin having high sweetness intensity from 4-(indol-3-ylmethyl)-4-hydroxy-2-oxoglutaric acid by substituting an amino acid at least at one of positions (positions 100, 180 to 183, 243 and 244) involved in efficiently producing the (2R, 4R)-monatin in an amino acid sequence of a wild-type D-aminotransferase represented in SEQ ID NO:2.

38 Claims, No Drawings

MUTATED D-AMINOTRANSFERASE AND METHOD FOR PRODUCING OPTICALLY ACTIVE GLUTAMIC ACID DERIVATIVES USING THE SAME

TECHNICAL FIELD

The present invention relates to a D-aminotransferase available for producing optically active glutamic acid derivatives, and particularly relates to a mutated D-aminotransferase obtained by mutation of a wild-type D-aminotransferase in a manner of amino acid substitution, which enables efficient production of (2R, 4R)-monatin from a monatin precursor. The present invention also relates to a method for producing a (2R, 4R) isomer of a glutamic acid derivative such as monatin and analogues thereof using the mutated D-aminotransferase.

BACKGROUND ART 4-(Indol-3-ylmethyl)-4-hydroxy-glutamic acid (3-(1-amino-1,3-dicarboxy-3-hydroxy-butane-4-yl)-indole) (hereinbelow referred to as "monatin") represented by the following structural formula (3) is present in roots of a plant *Schlerochitom ilicifolius* and is a particularly promising low-calorie sweetener because of its remarkably high sweetness intensity (JP 64-25757 A):

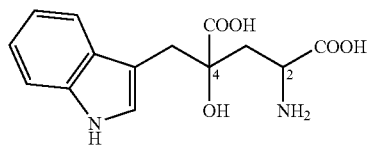

(3)

4-(Indol-3-ylmethyl)-4-hydroxy-glutamic acid

Monatin has two asymmetries at positions 2 and 4, and the natural stereoisomer has been reported to be a (2S, 4S) isomer. Other stereoisomers have been synthetically prepared, and three stereoisomers have been identified. It has been confirmed that any of them has sweetness intensity that is several ten to several thousand times higher than that of sucrose (Table 1).

TABLE 1

Sweetness of monatin isomers

| Stereoisomer | Sweetness (vs. sucrose) |
|---|---|
| 2R,4R | 2700 times |
| 2R,4S | 1300 times |
| 2S,4R | 300 times |
| 2S,4S | 50 times |

As is shown in Table 1, not only naturally occurring (2S, 4S)-monatin but also all other stereoisomers have the sweetness intensity with high scale factor. Particularly, (2R, 4R)-monatin has an remarkably high sweetness intensity which is 2,700 times higher than that of sucrose and is the most highly expected as a sweetening agent or a sweetening agent ingredient (sweetener). Therefore, it has been desired to develop a method for efficiently producing monatin with high content of (2R, 4R)-monatin.

Five examples of monatin production processes have been reported. Details thereof are described in (1) and (3) to (6) of the following prior art references.

(1) U.S. Pat. No. 5,994,559
(2) European Patent Publication No. 0736604 A
(3) Tetrahedron Letters, Vol. 42, No.39, pages 6793-6796, 2001
(4) Organic Letters, Vol. 2, No. 19, pages 2967-2970, 2000
(5) Synthetic Communication, Vol. 24, No. 22, pages 3197-3211, 1994
(6) Synthetic Communication, Vol. 23, No. 18, pages 2511-2526, 1993
(7) Taylor et al., Journal of Bacteriology, Vol. 180, No. 16, pages 4319, 1998

However, none of the aforementioned references refers to any stereoselective method for producing (2R, 4R)-monatin. In addition, all of the disclosed methods require multiple steps, which impedes practical production on an industrial scale.

In such a situation, the present inventors have proposed a novel method for producing monatin from 4-(indol-3-ylmethyl)-4-hydroxy-2-oxoglutaric acid (hereinbelow referred to as IHOG) using an enzymatic reaction shown in the following formula (4).

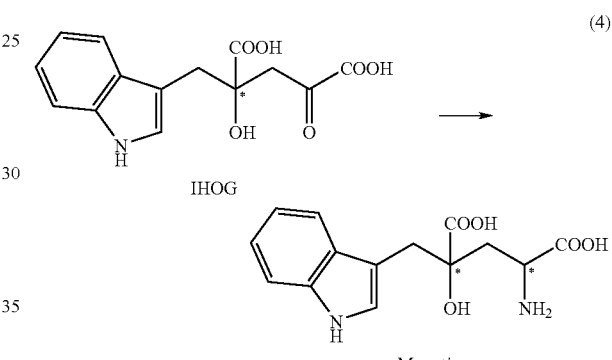

This novel method utilizes an enzyme which catalyzes an amination reaction at position 2 of a monatin precursor (IHOG), to thereby produce monatin from IHOG. Aminotransferase is one of enzymes which catalyze the amination reaction of IHOG. Employment of the D-aminotransferase results in selective production of 2R-monatin, and employment of a L-aminotransferase results in selective production of 2S-monatin. That is, employment of the D-aminotransferase as the enzyme for catalyzing the reaction results in selective production of the 2R isomer, i.e. the highly sweet isomer, as a result of transfer of an amino group from a D-amino acid as an amino donor to position 2 of IHOG.

Studies by the present inventors have revealed that the D-aminotransferase which catalyzes a reaction of the substrate IHOG to produce 2R-monatin is present in microorganisms belonging to genus *Bacillus* or *Paenibacillus*. However, even when using the D-aminotransferase derived from these microorganism, it has been difficult to efficiently produce monatin containing (2R, 4R)-monatin at a high ratio.

One of the reasons for such an inefficient (2R, 4R)-monatin production appears to be poor recognition of the asymmetry at position 4 of IHOG by the D-aminotransferase derived from these microorganisms. That is, when the D-aminotransferase derived from the microorganisms belonging to genus *Bacillus* or *Paenibacillus* is allowed to act upon a racemic mixture as to position 4 (sometimes abbreviated hereinbelow as 4R, S-IHOG), it acts upon both 4R-IHOG and 4S-IHOG and produces both (2R, 4R)-monatin and (2R, 4S)-monatin at an almost equal ratio. Thus, even when using the D-aminotransferase derived from these microorganisms, it has been impossible to produce monatin having an optical activity at position 4.

Another reason therefor would be instability of IHOG, the material for producing monatin, in a certain pH. In order to test stability of IHOG in the amination reaction of IHOG, the present inventors measured a change of IHOG concentration with time in an amination reaction solution of IHOG with no microbial cell addition. The reaction was performed by shaking a test tube containing 1 ml of reaction solution composed of 100 mM potassium phosphate buffer (pH 8.3), 300 mM 4R, S-IHOG, 600 mM DL-Ala and 1 mM pyridoxal-5'-phosphate at 37° C. for 40 hours. As a result, a residual ratio of 4R, S-IHOG was decreased to 81% after 16 hours, 70% after 24 hours and 57% after 40 hours, respectively. It was found that IHOG was decomposed with the lapse of time. It is presumed that this phenomenon is due to a decomposition reaction where IHOG is decomposed into 3-indole-pyruvic acid and pyruvic acid and a cyclization reaction of IHOG, to consume IHOG in the reaction solution before being converted to monatin. That is, the reaction catalyzed by the D-aminotransferase derived from the genus Bacillus or Paenibacillus is not sufficiently fast, and a part of IHOG becomes unavailable for the amination due to the decomposition and the cyclization before the amination. This is thought to be one reason why (2R, 4R) monatin can not be efficiently produced.

Accordingly, it has been desired to develop a method for efficiently producing (2R, 4R)-monatin which has the highest sweetness intensity among the monatin isomers.

A task to be accomplished by the present invention is to provide a D-aminotransferase capable of efficiently producing the (2R, 4R) isomer of the glutamic acid derivatives such as monatin and analogues thereof.

DISCLOSURE OF THE INVENTION

As a result of an extensive study to accomplish the above task, the present inventors have found out that a certain position in amino acid sequences of a D-aminotransferase derived from *Bacillus macerans* and of a D-aminotransferase derived from *Bacillus sphaericus* is involved in efficient production of (2R,4R) monatin, and that substitution of an amino acid residue at this specific position gives a D-aminotransferase capable of efficiently producing (2R, 4R)-monatin. The present inventors have completed the present invention based on these findings.

Among the positions involved in the efficient production of (2R, 4R)-monatin, the present inventors have further specified a position which acts upon a monatin precursor (IHOG) in a 4R-selective manner, and a position involved in enhancement of the amino group transfer activity of the D-aminotransferase.

That is, the D-aminotransferase of the present invention is a mutated aminotransferase modified to enable efficient production of (2R, 4R)-monatin by substituting some amino acid residues in a wild-type D-aminotransferase.

The wild-type D-aminotransferase has no optical selectivity with regard to the asymmetry at position 4 of IHOG, and therefore acts upon both 4R-IHOG and 4S-IHOG to produce (2R, 4R)-monatin and (2R, 4S)-monatin at an almost equal ratio. According to the present invention, however, substitution of a particular amino acid residue in the wild-type D-aminotransferase alters substrate specificity of the wild-type D-aminotransferase. Such a mutation lead to selective reaction of 4R-IHOG, resulting in selective conversion from 4R,S-IHOG to (2R, 4R)-monatin, and thus efficient production of (2R,4R) monatin.

The wild-type D-aminotransferase does not have a sufficient D-aminotransferase activity. Therefore, a part of IHOG becomes unavailable for the amination due to the decomposition reaction and the cyclization reaction before the amination, to cause inefficiency in the production of (2R, 4R)-monatin. However, in the present invention, a particular amino acid residue of the wild-type D-aminotransferase is substituted, to thereby enhance the D-aminotransferase activity. This substitution raises ratio of the amination rate of IHOG with respect to the decomposition and cyclization rate thereof, resulting in efficient production of (2R, 4R)-monatin.

The D-aminotransferase derived from *Bacillus macerans*, which is another aspect of the present invention, is a wild-type D-aminotransferase having an amino acid sequence described in SEQ ID NO:2. There has been no report as to the amino acid sequence of a D-aminotransferase derived from *Bacillus macerans*. The present inventors have isolated and purified the enzyme, and identified the amino acid sequence and a nucleotide sequence thereof for the first time. The D-aminotransferase derived from *Bacillus macerans* can be used suitably for producing 2R-monatin.

That is, the present invention is as follows:

[1] A protein comprising an amino acid sequence selected from the following (A) and (B):

(A) an amino acid sequence described in SEQ ID NO:2; and (B) an amino acid sequence having substitution, deletion, insertion, addition and/or inversion of one or several amino acid residues in the amino acid sequence described in SEQ ID NO:2;

wherein said protein has a D-aminotransferase activity.

[2] A protein comprising an amino acid sequence selected from the following (A) and (B):

(A) an amino acid sequence having substitution of an amino acid residue at least at one position selected from positions 100, 180 to 183, 243 and 244 in an amino acid sequence represented by SEQ ID NO:2; and (B) an amino acid sequence having substitution, deletion, insertion, addition and/or inversion of one or several amino acid residues at position(s) other than positions 100, 180 to 183, 243 and 244 in the amino acid sequence (A);

wherein said protein has a D-aminotransferase activity, and wherein an amount of (2R, 4R)-monatin produced with said protein from 4-(indol-3-ylmethyl)-4-hydroxy-2-oxoglutaric acid is greater than that produced with a protein having the amino acid sequence represented by SEQ ID NO:2.

[3] A protein comprising an amino acid sequence selected from the following (A) and (B):

(A) an amino acid sequence having at least one substitution of an amino acid residue selected from the following (a) to (e) in an amino acid sequence represented by SEQ ID NO:2:

(a) substitution of a serine residue at position 181 with another amino acid residue;

(b) substitution of an alanine residue at position 182 with another amino acid residue;

(c) substitution of an asparagine residue at position 183 with another amino acid residue;

(d) substitution of a serine residue at position 243 with another amino acid residue; and (e) substitution of a serine residue at position 244 with another amino acid residue; and (B) an amino acid sequence having substitution, deletion, insertion, addition and/or inversion of one or several amino acid residues at position(s) other than positions 181 to 183, 243 and 244 in the amino acid sequence (A);

wherein said protein has a D-aminotransferase activity to selectively act upon a 4R isomer of 4-(indol-3-ylmethyl)-4-hydroxy-2-oxoglutaric acid to produce (2R, 4R)-monatin.

[4] The protein according to [3], wherein said substitution selected from (a) to (e) is any one of the following substitutions (a') to (e'):

(a') substitution of the serine residue at position 181 with an asparagine residue;

(b') substitution of the alanine residue at position 182 with a lysine or serine residue;

(c') substitution of the asparagine residue at position 183 with a serine residue;

(d') substitution of the serine residue at position 243 with a glutamic acid, leucine, lysine, asparagine or glutamine residue; and (e') substitution of the serine residue at position 244 with a lysine residue.

[5] A protein comprising an amino acid sequence selected from the following (A) and (B):

(A) an amino acid sequence having substitution of at least one amino acid residue selected from the following (a) to (c) in an amino acid sequence represented by SEQ ID NO:2:
  (a) substitution of an asparagine residue at position 100 with another amino acid residue;
  (b) substitution of a serine residue at position 181 with another amino acid residue; and
  (c) substitution of an alanine residue at position 182 with another amino acid residue; and (B) an amino acid sequence having substitution, deletion, insertion, addition and/or inversion of one or several amino acid residues at position(s) other than positions 100, 181 and 182 in the amino acid sequence (A);

wherein said protein has a D-aminotransferase activity, and wherein said D-aminotransferase activity of said protein to produce 2R-monatin from 4-(indol-3-ylmethyl)-4-hydroxy-2-oxoglutaric acid is higher than that of a protein having the amino acid sequence represented by SEQ ID NO:2.

[6] The protein according to [5], wherein said substitution selected from (a) to (c) is any one of the following substitutions (a') to (c'):

(a') substitution of the asparagine residue at position 100 with an alanine residue;

(b') substitution of the serine residue at position 181 with an alanine residue; and (c') substitution of the alanine residue at position 182 with a serine residue.

[7] A protein comprising an amino acid sequence having substitution selected from any one of the following (i) to (vii) in an amino acid sequence represented by SEQ ID NO:2:

(i) substitution of a serine residue at position 243 with an asparagine residue;

(ii) substitution of a serine residue at position 244 with a lysine residue;

(iii) substitution of a serine residue at position 180 with an alanine residue and substitution of a serine residue at position 243 with an asparagine residue;

(iv) substitution of a serine residue at position 180 with an alanine residue and substitution of a serine residue at position 244 with a lysine residue;

(v) substitution of a serine residue at position 243 with an asparagine residue and substitution of a serine residue at position 244 with a lysine residue;

(vi) substitution of an asparagine residue at position 100 with an alanine residue and substitution of a serine residue at position 243 with an asparagine residue; and (vii) substitution of an alanine residue at position 182 with a serine residue and substitution of a serine residue at position 243 with an asparagine residue.

[8] A protein comprising an amino acid sequence selected from the following (A) and (B):

(A) an amino acid sequence having at least one substitution of an amino acid residue selected from the following (a) and (b) in an amino acid sequence represented by SEQ ID NO:4:
  (a) substitution of a serine residue at position 243 with another amino acid residue; and
  (b) substitution of a serine residue at position 244 with another amino acid residue; and (B) an amino acid sequence having substitution, deletion, insertion, addition and/or inversion of one or several amino acid residues at position(s) other than positions 243 and 244 in the amino acid sequence (A);

wherein said protein has a D-aminotransferase activity to selectively act upon a 4R isomer of 4-(indol-3-ylmethyl)-4-hydroxy-2-oxoglutaric acid to produce (2R, 4R)-monatin.

[9] The protein according to [8], wherein said substitution selected from (a) and (b) is any one of the following substitutions (a') and (b'):

(a') substitution of the serine residue at position 243 with a lysine or asparagine residue; and (b') substitution of the serine residue at position 244 with a lysine residue.

[10] A method for producing an optically active glutamic acid derivative, comprising reacting a keto acid represented by the following general formula (1):

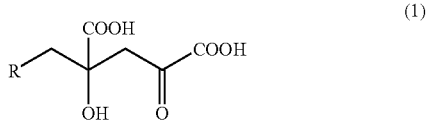

in the presence of the protein according to any one of [2] to [9] and an amino donor, to generate a (2R,4R) isomer of said glutamic acid derivative represented by the following general formula (2):

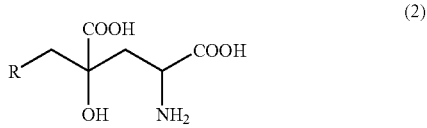

or a salt thereof;

wherein R in the formulae (1) and (2) is an aromatic or heterocyclic ring, and said aromatic or heterocyclic ring may further have one or more substituents chosen from a halogen atom, a hydroxyl group, an alkyl group having up to 3 carbon atoms, an alkoxy group having up to 3 carbon atoms, and an amino group.

[11] The method for producing the optically active glutamic acid derivative according to [10], wherein said R is a phenyl or indolyl group.

[12] The method for producing the optically active glutamic acid derivative according to [10] or [11], wherein said amino donor is an amino acid.

[13] The method for producing the optically active glutamic acid derivative according to [12], wherein said reaction is performed in a reaction system further containing an enzyme having an activity to catalyze a reaction for converting an L-amino acid to a D-amino acid, or a microorganism having such an enzymatic activity.

[14] A DNA comprising a nucleotide sequence selected from the following (A) and (B):
    (A) a nucleotide sequence described in SEQ ID NO:1; and
    (B) a nucleotide sequence which hybridizes under a stringent condition with another DNA composed of a nucleotide sequence complementary to the nucleotide sequence described in SEQ ID NO:1;
    wherein said DNA encodes a protein having a D-aminotransferase activity.

[15] A DNA encoding a protein having an amino acid sequence selected from the following (A) and (B):
    (A) an amino acid sequence described in SEQ ID NO:2; and
    (B) an amino acid sequence having substitution, deletion, insertion, addition and/or inversion of one or several amino acid residues in the amino acid sequence described in SEQ ID NO:2;
    wherein said protein has a D-aminotransferase activity.

[16] A DNA encoding a protein having an amino acid sequence selected from the following (A) and (B):
    (A) an amino acid sequence having substitution of an amino acid residue at least at one position selected from positions 100, 180 to 183, 243 and 244 in an amino acid sequence represented by SEQ ID NO:2; and
    (B) an amino acid sequence having substitution, deletion, insertion, addition and/or inversion of one or several amino acid residues at position(s) other than positions 100, 180 to 183, 243 and 244 in the amino acid sequence (A);
    wherein said protein has a D-aminotransferase activity, and wherein an amount of (2R, 4R)-monatin produced with said protein from 4-(indol-3-ylmethyl)-4-hydroxy-2-oxoglutaric acid is greater than that produced with a protein having the amino acid sequence represented by SEQ ID NO:2.

[17] A DNA encoding a protein having an amino acid sequence selected from the following (A) and (B):
    (A) an amino acid sequence having substitution of at least one amino acid residue selected from the following (a) and (b) in an amino acid sequence represented by SEQ ID NO:4:
        (a) substitution of a serine residue at position 243 with another amino acid residue; and
        (b) substitution of a serine residue at position 244 with another amino acid residue; and
    (B) an amino acid sequence having substitution, deletion, insertion, addition and/or inversion of one or several amino acid residues at position(s) other than positions 243 and 244 in the amino acid sequence (A);
    wherein said protein has a D-aminotransferase activity to selectively act upon a 4R isomer of 4-(indol-3-ylmethyl)-4-hydroxy-2-oxoglutaric acid to produce (2R, 4R)-monatin.

[18] A recombinant DNA obtained by ligating the DNA according to any one of [14] to [17] to a vector DNA.

[19] A cell transformed with the recombinant DNA according to [18].

[20] A method for producing a protein having a D-aminotransferase activity, comprising culturing the cell according to [19] in a medium and accumulating said protein having said D-aminotransferase activity in said medium and/or said cell.

PREFERRED EMBODIMENTS FOR CARRYING OUT THE INVENTION

The present inventors have determined an amino acid sequence (SEQ ID NO:2) of a D-aminotransferase derived from genus *Bacillus*, which catalyzes a reaction to produce 2R-monatin from IHOG. As a result of further studies, the present inventors have found out that positions 100, 180 to 183, 243 and 244 in the amino acid sequence represented by SEQ ID NO:2 are involved in efficient production of (2R, 4R)-monatin.

As a result of further several studies, they have demonstrated that, among the sites involved in efficient production of (2R, 4R)-monatin, a region of positions 181 to 183 and positions 243 to 244 are involved in steric recognition of position 4 in IHOG, and that positions 100, 181 and 182 are involved in enhancing the D-aminotransferase activity. Furthermore, they have demonstrated that substitution at position 180 in combination with substitution of the amino acid residue that is involved in 4R isomer selectivity leads to suppression of the D-aminotransferase activity reduction.

The present invention will be described in detail in the following order

[A] Mutated D-aminotransferase
    [I] Amino acid sequences of mutated D-aminotransferase
        (i) Mutated D-aminotransferase derived from *Bacillus macerans*
        (ii) Mutated D-aminotransferase derived from *Bacillus sphaericus*
    [II] Method for producing mutated D-aminotransferase
        (i) Obtaining wild-type D-aminotransferase gene
        (ii) Preparation of mutated D-aminotransferase gene
        (iii) Production and cultivation of bacteria which produce mutated D-aminotransferase

[B] Method for Producing (2R, 4R)Glutamic Acid Derivative Using Mutated D-aminotransferase
    [I] D-aminotransferase
    [II] Substrate keto acid
    [III] Amino donor
    [IV] Reaction conditions

[A] Mutated D-aminotransferase

The mutated D-aminotransferase of the present invention is a D-aminotransferase obtained by substituting a part of amino acid residues of the D-aminotransferase derived from genus *Bacillus*, which catalyzes a reaction to produce 2R-monatin from IHOG represented by the following formula (5). The mutated D-aminotransferase of the present invention is characterized in that an amino acid residue of a part of the wild-type D-aminotransferase is substituted to realize efficient production of (2R, 4R)-monatin.

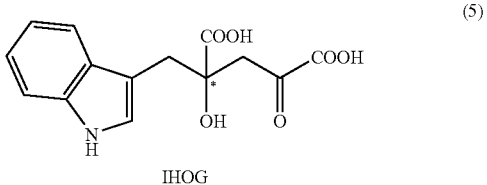

IHOG

As used herein, "D-aminotransferase" means an enzyme which produces 2R-monatin by transferring an amino group of a D-amino acid as an amino donor to IHOG.

The mutated D-aminotransferase of the present invention is a modified product so as to efficiently produce (2R, 4R) monatin, and is broadly classified into (1) those modified so as to act 4R-selectively upon IHOG and (2) those modified so as to enhance the D-aminotransferase activity. The mutated D-aminotransferase that has been modified so as to act 4R-selectively upon IHOG and to enhance the D-aminotransferase activity as well is of course within the scope of the present invention.

"Act 4R-selectively" in the definition of the aforementioned class (1) means that 4R-monatin is produced at a ratio of more than 53% based on a total amount of produced monatin as a result of the monatin production with 4R,S-IHOG as a substrate. "4R-selectivity" means a property to act 4R-selectively. The ratio of 4R-monatin based on the total amount of the monatin production is preferably not less than 55%, more preferably not less than 60%, still more preferably not less than 80%, and particularly preferably not less than 90%.

In some cases, the mutated D-aminotransferase of the present invention may have selectivity for the 4R isomer of not only the monatin precursor (IHOG) but also a keto acid represented by the following general formula (1):

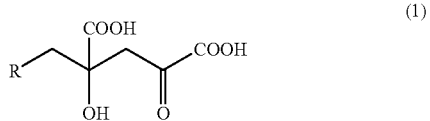

wherein R is an aromatic or heterocyclic ring, and the aromatic or heterocyclic ring may further have one or more substituents chosen from a halogen atom, a hydroxyl group, an alkyl group having up to 3 carbon atoms, an alkoxy group having up to 3 carbon atoms and an amino group.

The wild-type D-aminotransferase as it is can not discriminate optical isomerism of IHOG that is the monatin precursor, and acts upon both 4S and 4R isomers to produce (2R, 4R)-monatin and (2R, 4S)-monatin at almost equal ratio. However, the mutated D-aminotransferase (1) is a modified product obtained by substituting the amino acid residue of a part of the wild-type D-aminotransferase to alter substrate specificity thereof. Therefore the mutated D-aminotransferase (1) acts 4R-selectively upon IHOG, which enables selective production of (2R, 4R)-monatin from IHOG.

"To enhance the D-aminotransferase activity" in the definition of the aforementioned class (2) means that the D-aminotransferase activity is enhanced when compared to that of the wild-type D-aminotransferase, which results in the increased amount of 2R-monatin production from IHOG. Specifically in the example of the reaction with the protein of SEQ ID NO:2, the requirement is satisfied if the amount of 2R-monatin produced from 4R, S-IHOG is greater than that produced with the D-aminotransferase derived from *Bacillus macerans*. The amount of 2R-monatin production is preferably 1.1 times, more preferably 1.2 times, still more preferably 1.5 times and particularly preferably 2 times or more greater than that obtained in the same reaction conditions with the D-aminotransferase derived from *Bacillus macerans* represented by SEQ ID NO:2.

In an enzymatic reaction in most of cases, enhancement of an enzymatic activity merely accelerates the reaction rate but does not alter the amount of products. However, IHOG, the material of monatin, is an unstable compound as explained above. It is thought that the decomposition reaction of IHOG to be 3-indole-pyruvic acid and pyruvic acid and the cyclization reaction of IHOG occur in a reaction liquid. The enhancement of the D-aminotransferase activity may lead to acceleration of the relative rate of the amination with respect to the decomposition and cyclization of IHOG, which therefore results in efficient production of (2R, 4R)-monatin. Example of the methods for conveniently measuring the amination reaction rate of the D-aminotransferase may include a measurement of the amino group transfer activity with D-Ala and α-ketoglutaric acid as substrates. Such a measurement may be carried out by enzymatically analyzing pyruvic acid produced as the reaction proceeds, using lactate dehydrogenase.

[I] Amino Acid Sequence of Mutated D-aminotransferase

The wild-type D-aminotransferase from which the mutated D-aminotransferase of the present invention has been derived may be the D-aminotransferase derived from the genus *Bacillus*, which catalyzes the reaction to produce 2R-monatin from IHOG. Examples of such a D-aminotransferase may include a D-aminotransferase derived from *Bacillus macerans* and a D-aminotransferase derived from *Bacillus sphaericus*.

The mutated D-aminotransferase of the present invention will hereinbelow be classified into the mutated D-aminotransferase derived from *Bacillus macerans* and the mutated D-aminotransferase derived from *Bacillus sphaericus*, and the amino acid sequences thereof will be explained separately.

(I-1) Mutated D-aminotransferase Derived from *Bacillus macerans*

The wild-type D-aminotransferase derived from *Bacillus macerans* AJ1617 has an amino acid sequence represented by SEQ ID NO:2.

(1) Amino Acid Substitution at Positions Involved in 4R-Selectivity

A region of positions 181 to 183 and a region of positions 243 to 244 in the amino acid sequence described in SEQ ID NO:2 are sites involved in steric recognition of position 4 in IHOG.

That is, the D-aminotransferase derived from *Bacillus macerans* may be modified so as to act 4R-selectively upon IHOG by substituting an amino acid residue at least at one of positions 181 to 183 and 243 to 244 with another amino acid residue in the amino acid sequence described in SEQ ID NO:2. The amino acid substitution at the position involved in the 4R-selectivity may be performed at one position or two more positions.

When a serine residue at position 181 is substituted with an amino acid residue, it is preferable that the residue is substituted with an asparagine residue. When an alanine residue at position 182 is substituted with an amino acid residue, it is preferable that the residue is substituted with a lysine or serine residue. When an asparagine residue at position 183 is substituted with an amino acid residue, it is preferable that the residue is substituted with a serine residue. When a serine residue at position 243 is substituted with an amino acid residue, it is preferable that the residue is substituted with a glutamic acid, leucine, lysine, asparagine or glutamine residue, and particularly with the asparagine residue. When a serine residue at position 244 is substituted with an amino acid residue, it is preferable that the residue is substituted with a lysine residue.

Among the substitutions at the positions involved in the 4R-selectivity, the amino acid substitution at position 243 or 244 is particularly preferable because the 4R-selectivity can often be effectively enhanced. The amino acid substitution of the amino acids at both positions 243 and 244 is more preferable because the 4R-selectivity can further be enhanced.

As described above, the 4R-selectivity for IHOG may be imparted by substituting the amino acid residue at least at one of positions 181 to 183 and 243 to 244 with another amino acid residue in the amino acid sequence represented by SEQ ID NO:2. However, even when the amino acid sequence has a substitution, deletion, insertion, addition and/or inversion of one or several amino acid residues at the position(s) other than the positions involved in the 4R-selectivity, i.e., other than positions 181 to 183 and 243 to 244, the protein still falls in the scope of the mutated D-aminotransferase of the present invention as long as the protein has the D-aminotransferase activity to act 4R- selectively upon IHOG to produce (2R, 4R)-monatin.

As used herein, "one or several" is within the range where a three-dimensional structure of the protein, the D-aminotransferase activity and the 4R-selectivity for IHOG are not significantly impaired by the relevant substitution of the amino acid residues, and is specifically 1 to 50, preferably 1 to 30, more preferably 1 to 20, and particularly preferably 1 to 10. However, in the case of the amino acid sequence including the substitution, deletion, insertion, addition and/or inversion of one or several amino acid residues in the amino acid sequence described in SEQ ID NO:2, it is preferable that the protein having the sequence retains the D-aminotransferase activity at not less than 3%, preferably not less than 10%, more preferably not less than 30%, still more preferably not less than 50% and particularly preferably not less than 70% compared to that of the protein having the amino acid sequence described in SEQ ID NO:2 under the conditions of 30° C. and pH 8.0.

(2) Substitution at Positions Involved in Enhancement of D-aminotransferase Activity Positions 100, 181 and 182 in the amino acid sequence described in SEQ ID NO:2 are positions involved in the enhancement of the D-aminotransferase activity.

That is, the D-aminotransferase derived from *Bacillus macerans* may be modified so as to enhance the D-aminotransferase activity by substituting the amino acid residue at least at one of positions 100, 181 and 182 with another amino acid residue in the amino acid sequence described in SEQ ID NO:2. The amino acid substitution at the position involved in the enhancement of the D-aminotransferase activity may be performed at one position or two or more positions.

When the asparagine residue at position 100 is substituted with an amino acid residue, it is preferable that the residue is substituted with an alanine residue. When the serine residue at position 181 is substituted with an amino acid residue, it is preferable that the residue is substituted with an alanine residue. When the alanine residue at position 182 is substituted with an amino acid residue, it is preferable that the residue is substituted with a serine residue.

Substitution at two or more positions in combination among the positions involved in the enhancement of the D-aminotransferase activity is more preferable because the D-aminotransferase activity may be still more enhanced.

As described above, the D-aminotransferase activity may be enhanced by substituting the amino acid residue at least at one of positions 100, 181 and 182 in the amino acid sequence represented by SEQ ID NO:2 with another amino acid residue. However, even when the amino acid sequence has a substitution, deletion, insertion, addition and/or inversion of one or several amino acid residues at the position(s) other than the positions involved in the enhancement of the D-aminotransferase activity, i.e., other than positions 100, 181 and 182, the protein still falls in the scope of the mutated D-aminotransferase of the present invention as long as the protein has a higher D-aminotransferase activity to produce 2R-monatin from IHOG than that of the D-aminotransferase derived from *Bacillus macerans* represented by SEQ ID NO:2.

As used herein, "one or several" is within the range where a three-dimensional structure of the protein, the D-aminotransferase activity and the 4R-selectivity for IHOG are not significantly impaired by the relevant substitution of the amino acid residues, and is specifically 1 to 50, preferably 1 to 30, more preferably 1 to 20, and particularly preferably 1 to 10. However, in the case of the amino acid sequence including the substitution, deletion, insertion, addition and/or inversion of one or several amino acid residues, it is desirable that the protein having the sequence retains the D-aminotransferase activity at more than 100%, preferably not less than 110%, more preferably not less than 120%, still more preferably not less than 150% and particularly preferably not less than 200% compared to that of the protein having the amino acid sequence described in SEQ ID NO:2 under a conditions of 30° C. and pH 8.0.

(3) D-aminotransferase Capable of Efficiently Producing (2R, 4R)-monatin

In the present invention, it is preferable that the D-aminotransferase capable of producing an enhanced amount of (2R,4R)-monatin from IHOG is prepared by substituting the amino acid residue at least at either one of the positions involved in the 4R-selectivity described in the above (1) and the positions involved in the enhancement of the D-aminotransferase activity described in the above (2).

"Producing an enhanced amount of (2R, 4R)-monatin from IHOG" means that the amount of (2R, 4R)-monatin produced therewith from IHOG is enhanced when compared to that produced with the wild-type D-aminotransferase. Specifically in the example of the reaction with the protein of SEQ ID NO:2, the requirement is satisfied if the amount of (2R, 4R)-monatin produced from 4R, S-IHOG is greater than that produced with the D-aminotransferase derived from *Bacillus macerans* under the same conditions. The amount of (2R, 4R)-monatin production is preferably 1.1 times, more preferably 1.2 times, still more preferably 1.5 times and particularly preferably 2 times or more greater than that obtained with the D-aminotransferase derived from *Bacillus macerans* represented by SEQ ID NO:2.

Example of the method for conveniently measuring the amination reaction rate of the D-aminotransferase may include a measurement of the amino group transfer activity with D-Ala and α-ketoglutaric acid as substrates. Such a measurement may be carried out by enzymatically analyzing pyruvic acid produced as the reaction proceeds, using lactate dehydrogenase.

In order to produce the D-aminotransferase capable of efficiently producing (2R, 4R)-monatin, it is preferable that the amino acid substitution at the position involved in the 4R-selectivity described in the above (1) is carried out in combination with the amino acid substitution at the position involved in the enhancement of the D-aminotransferase activity described in the above (2).

If the amino acid substitution is introduced at only one of the position involved in the 4R-selectivity described in the above (1) and the position involved in the enhancement of the D-aminotransferase activity described in the above (2), balance of these enzymatic activities may become worse in some cases. That is, when the amino acid substitution is introduced only at the position involved in the 4R-selectivity, the 4R-selectivity may be enhanced but the D-aminotransferase activity may be reduced (the yield of 2R-monatin production may be reduced). Conversely, when the amino acid substitution is introduced only at the position involved in the enhancement of the D-aminotransferase, the 4R-selectivity may be sometimes reduced. However, by appropriately combining these substitutions, the D-aminotransferase having the 4R-selectivity and the D-aminotransferase activity in an well-balanced manner in total may be produced.

Specifically, it is preferable to combine the substitution at position 100 or 182 with the substitution at position 243. Such substitution gives a mutated D-aminotransferase having an excellent 4R-selectivity and D-aminotransferase activity.

Substitution at position 180 in combination with the substitution of the amino acid residue at the position involved in the 4R-selectivity is also preferable because the reduction of the D-aminotransferase activity may be inhibited thereby. In this case, it is preferable to substitute the serine residue at position 180 with the alanine residue. The introduction of a mutation at position 180 may enhance the yield of monatin when combined with the amino acid substitution at the position involved in the 4R-selectivity. In particular, it is preferable to combine the amino acid substitution at positions 243 and/or 244 with the amino acid substitution at position 180.

As described above, the mutated D-aminotransferase capable of efficiently producing (2R, 4R)-monatin may be obtained by substituting the amino acid residue at least at one of positions 100, 180 to 183, 243 and 244 with another amino acid residue in the amino acid sequence represented by SEQ ID NO:2. However, even when the amino acid sequence has a substitution, deletion, insertion, addition and/or inversion of one or several amino acid residues at the position(s) other than the position involved in the mutation for efficient production of (2R, 4R)-monatin, i.e., other than positions 100, 180 to 183, 243 and 244, the protein still falls in the scope of the mutated D-aminotransferase of the present invention as long as the protein has a higher D-aminotransferase activity to produce (2R, 4R)-monatin from 4-(indol-3-ylmethyl)-4-hydroxy-2-oxoglutaric acid than that of the D-aminotransferase derived from *Bacillus macerans* represented by SEQ ID NO:2.

As used herein, "one or several" is within the range where a three-dimensional structure of the protein, the D-aminotransferase activity and the 4R-selectivity for IHOG are not significantly impaired by the relevant substitution of the amino acid residues, and is specifically 1 to 50, preferably 1 to 30, more preferably 1 to 20, and particularly preferably 1 to 10. However, in the case of the amino acid sequence including the substitution, deletion, insertion, addition and/or inversion of one or several amino acid residues, it is desirable that the D-aminotransferase activity to produce (2R, 4R)-monatin from 4-(indol-3-ylmethyl)-4-hydroxy-2-oxoglutaric acid is more than 100%, preferably not less than 110%, more preferably not less than 120%, still more preferably not less than 150% and particularly preferably not less than 200% compared to that of the protein having the amino acid sequence described in SEQ ID NO:2 under the conditions of 30° C. and pH 8.0.

(I-2) Mutated D-aminotransferase Derived From *Bacillus sphaericus*

The wild-type D-aminotransferase derived from *Bacillus sphaericus* ATCC 10208 has an amino acid sequence represented by SEQ ID NO:4. A D-aminotransferase gene derived from *Bacillus sphaericus* has been reported in Patent Document (2) and Non-Patent Document (5). As described above, it has been predicted that the D-aminotransferase derived from *Bacillus sphaericus* ATCC 10208 has the positions involved in the 4R-selectivity at positions 243 and 244 which are common to the D-aminotransferase derived from *Bacillus macerans*.

That is, the D-aminotransferase may be modified so as to act 4R-selectively upon IHOG by substituting the amino acid residue at least at one of positions 243 and 244 in the amino acid sequence described in SEQ ID NO:4 with another amino acid residue. The amino acid substitution at the position involved in the 4R-selectivity may be performed at one position or two or more positions.

When the serine residue at position 243 is substituted with an amino acid residue, it is preferable that the residue is substituted with a lysine or asparagine residue. When the serine residue at position 244 is substituted with the amino acid residue, it is preferable that the residue is substituted with a lysine residue.

As described above, the mutated D-aminotransferase derived from *Bacillus sphaericus* of the present invention has the substitution of the amino acid residue at least at one position of positions 243 and 244 in the amino acid sequence represented by SEQ ID NO:4 with another amino acid residue, to thereby obtain 4R-selectivity for IHOG. However, even when the amino acid sequence has a substitution, deletion, insertion, addition and/or inversion of one or several amino acid residues at the position(s) other than the position involved in the 4R-selectivity of the mutated D-aminotransferase derived from *Bacillus sphaericus* (such as positions 243 and 244), the protein still falls in the scope of the mutated D-aminotransferase of the present invention as long as the protein has the D-aminotransferase activity to act 4R-selectively upon IHOG to produce (2R, 4R)-monatin.

As used herein, "one or several" is within the range where a three-dimensional structure of the protein, the D-aminotransferase activity and the 4R-selectivity for IHOG are not significantly impaired by the relevant substitution of the amino acid residues, and is specifically 1 to 50, preferably 1 to 30, more preferably 1 to 20, and particularly preferably 1 to 10. However, in the case of the amino acid sequence including the substitution, deletion, insertion, addition and/or inversion of one or several amino acid residues in the amino acid sequence described in SEQ ID NO:4, it is preferable that the protein having the sequence retains the D-aminotransferase activity at not less than 3%, preferably not less than 10%, more preferably not less than 30%, still more preferably not less than 50% and particularly preferably not less than 70% compared to that of the protein having the amino acid sequence described in SEQ ID NO:4 under the conditions of 30° C. and pH 8.0.

As in the above, the mutated D-aminotransferase of the present invention was classified into the mutated D-aminotransferase derived from *Bacillus macerans* and the mutated D-aminotransferase derived from *Bacillus sphaeri-* cus, and each class has been described separately. However, the present invention is not limited thereto. That is, a modified D-aminotransferase derived from other species belonging to the genus *Bacillus* which catalyzes the reaction to produce 2R-monatin from IHOG may fall within the scope of the mutated D-aminotransferase of the present invention, if the mutation is the amino acid substitution at the position corresponding to the position involved in the efficient production of (2R, 4R)-monatin described as to *Bacillus macerans* and *Bacillus sphaericus* (i.e., at positions 100, 180 to 183, 243 to 244), so as to efficiently produce (2R, 4R)-monatin from IHOG.

[II] Method for Producing Mutated D-aminotransferase

The mutated D-aminotransferase of the present invention may be produced by obtaining a gene encoding the wild-type D-aminotransferase which catalyzes the reaction to produce 2R-monatin from IHOG; introducing mutation thereinto so that the amino acid residue at the position involved in the efficient production of (2R, 4R)-monatin is substituted, to thereby prepare a mutated D-aminotransferase gene; and expressing the mutated gene in an appropriate host.

The production may also be performed by obtaining the mutated D-aminotransferase gene derived from a mutant strain which produces the mutated D-aminotransferase, and expressing the gene in an appropriate host (II-1) Obtaining Wild-Type D-aminotransferase Gene A DNA fragment containing a structural gene encoding a protein having the D-aminotransferase activity which catalyzes the reaction to produce the 2R-monatin from IHOG may be cloned from cells of, e.g. microorganisms, having such an enzyme activity.

Bacteria having the D-aminotransferase activity which catalyzes the reaction to produce 2R-monatin from IHOG may include bacteria belonging to the genus *Bacillus*, and may more specifically include the following bacterial strains:

*Bacillus macerans* AJ1617,

*Bacillus sphaericus* ATCC 10208,

*Bacillus pulvifaciens* AJ1327,

*Bacillus lentus* AJ12699 and

*Bacillus lentus* ATCC 10840.

*Bacillus macerans* AJ1617 has been deposited as follows.

(i) Name and address of the depositary authority

Name: International Patent Organism Depositary, National Institute of Advanced Industrial Science and Technology Address: Central 6, 1-1-1 Higashi, Tsukuba-shi, Ibaraki Prefecture, 305-8566, Japan (ii) Date of deposit: Dec. 13, 2001

(iii) Accession number FERM BP-8243 (transferred to the International Deposition on Nov. 22, 2002, from FERM P-18653 that had been deposited on Dec. 13, 2001)

Among them, *Bacillus macerans* and *Bacillus sphaercus* are preferable, and in particular *Bacillus macerans* AJ1617 and *Bacillus sphaericus* ATCC 10208 are preferable.

A DNA encoding the D-aminotransferase derived from *Bacillus macerans* AJ1617 strain is shown as SEQ ID NO:1. A DNA encoding the D-aminotransferase derived from *Bacillus sphaericus* ATCC 10208 strain is shown as SEQ ID NO:3.

The D-aminotransferase gene derived from *Bacillus macerans* AJ1617 strain has 91% and 83.6% homology with the D-aminotransferase gene derived from *Bacillus sphaedcus* ATCC 10208 strain in terms of the amino acid sequence and nucleotide sequence, respectively, 66% homology in terms of the amino acid sequence with the D-aminotransferase gene derived from *Bacillus sp.* YM-1 strain, and 42% homology in terms of the amino acid sequence with the D-aminotransferase gene derived from *Bacillus licheniformis* ATCC 10716 strain (these homologies were calculated with gene analysis software "genetyx ver. 6" (Genetyx) with default parameters.).

The DNA encoding the D-aminotransferase derived from *Bacillus macerans* AJ1617 strain described in SEQ ID NO:1, whose nucleotide sequence has been identified for the first time by the present inventors, belongs to the present invention. A DNA which hybridizes with a DNA composed of a nucleotide sequence complementary to the nucleotide sequence described in SEQ ID NO:1 under a stringent condition and encodes a protein having the D-aminotransferase activity also belongs to the present invention. As used herein, the "stringent condition" refers to a condition wherein a so-called specific hybrid is formed whereas a non-specific hybrid is not formed. Although it is difficult to clearly show this condition with numerical figure, one example of the condition may be the condition wherein a pair of DNA sequences having high homology, for example, more than 85%, preferably more than 90% and particularly preferably 95% or more homology are hybridized whereas DNA sequences with lower homology than that are not hybridized (it is desirable that the homology referred to herein is the value calculated with alignment such that the number of matched nucleotides between the compared sequences is maximized.). Another example thereof may be a washing condition for an ordinary Southern hybridization, i.e., hybridization at salt concentrations equivalent to 37° C., 0.1×SSC and 0.1% SDS, preferably 60° C., 0.1×SSC and 0.1% SDS, more preferably 65° C., 0.1×SSC and 0.1% SDS. However, as to the nucleotide sequence which hybridizes with the nucleotide sequence complementary to the nucleotide sequence described in SEQ ID NO: 1 under the stringent condition, it is desirable that the encoded protein retains the D-aminotransferase activity at not less than 10%, preferably not less than 30%, more preferably not less than 50% and still more preferably not less than 70% compared to that of the protein having the amino acid sequence described in SEQ ID NO:2 under the conditions of 30° C. and pH 8.0.

The amino acid sequence of the D-aminotransferase derived from *Bacillus macerans* AJ 1617 strain which the nucleotide sequence of SEQ ID NO:1 encodes is shown in SEQ ID NO:2. SEQ ID NO:2 is the amino acid sequence of the D-aminotransferase encoded by the nucleotide sequence of nucleotide numbers 630 to 1481 in the nucleotide sequence described in SEQ ID NO:1. The amino acid sequence of the D-aminotransferase derived from *Bacillus macerans* AJ1617 strain has been identified for the first time by the present inventors, which also belongs to the present invention. Even when the amino acid sequence has the substitution, deletion, insertion, addition and/or inversion of one or several amino acid residues in the amino acid sequence described in SEQ ID NO:2, the protein still falls in the scope of the present D-aminotransferase derived from *Bacillus macerans* as long as the protein has the D-aminotransferase activity. As used herein, "one or several" is within the range where the three-dimensional structure of the protein, and the D-aminotransferase activity is not significantly impaired by the relevant substitution of the amino acid residues, and is specifically 1 to 20, preferably 1 to 10, more preferably 1 to 5. As used herein, the "D-aminotransferase activity" means an activity to produce 2R-monatin by transferring an amino group of a D-amino acid as an amino donor to IHOG. In the case of the amino acid sequence including the substitution, deletion, insertion, addition and/or inversion of one or several amino acid residues in the amino acid sequence described in SEQ ID NO:2, it is desirable that the protein having the sequence retains the D-aminotransferase activity at not less than 10%, preferably not less than 30%, more preferably not less than 50% and still more preferably not less than 70% compared to that of the protein having the amino acid sequence described in SEQ ID NO:2 under the conditions of 30° C. and pH 8.

Subsequently, a method for obtaining a DNA encoding the wild-type D-aminotransferase from the bacteria which produce the D-aminotransferase will be described.

First, the amino acid sequence of the purified D-aminotransferase is determined. The determination of the amino acid sequence may be performed with Edman method (Edman, P., Acta Chem. Scad., 4:227, 1950). The amino acid sequence may also be determined with a sequencer supplied from Applied Biosystems.

On the basis of the determined amino acid sequence, the nucleotide sequence of the DNA encoding the amino acid sequence may be deduced. To deduce the DNA nucleotide sequence, the universal codons may be employed.

In accordance with the deduced nucleotide sequence, a DNA molecule of about 30 nucleotide pairs is synthesized. The method for synthesizing the DNA molecule is disclosed in Tetrahedron Letters, 22: p1859, 1981. The DNA molecule may also be synthesized with a synthesizer supplied from Applied Biosystems. The DNA molecule may be utilized as a probe when the full length DNA encoding the D-aminotransferase is isolated from a chromosomal gene library of the bacteria which produce the D-aminotransferase. The molecule may also be utilized as a primer when the DNA encoding the D-aminotransferase of the present invention is amplified by PCR method. However, the DNA amplified with the PCR method does not include the full length DNA encoding the D-aminotransferase. Therefore, with the use of the DNA amplified using the PCR method as a probe, the full length DNA encoding the D-aminotransferase is isolated from the chromosomal gene library of the bacteria which produce the D-aminotransferase.

The PCR method is described in White, T. J. et al., Trend Genet., 5: p185, 1989. The method for preparing the chromosomal DNA and the method for isolating the target DNA molecule from the gene library using a DNA molecule as a probe are described in Molecular Cloning, 2nd edition (Cold Spring Harbor Press, 1989).

The method for determining the isolated nucleotide sequence of the DNA encoding the D-aminotransferase is described in A Practical Guide to Molecular Cloning (John Wily & Sons, Inc., 1985). The nucleotide sequence may also be determined with the DNA sequencer supplied from Applied Biosystems.

(II-2) Preparation of Mutated D-aminotransferase Gene

The wild-type D-aminotransferase obtained from the bacteria which produce the D-aminotransferase can not discriminate the optical isomerism of IHOG which is the precursor of monatin, and acts upon both the 4S and 4R-isomers of IHOG to produce (2R, 4R)-monatin and (2R, 4S)-monatin at an almost equal amount. Besides, the amination reaction rate is not sufficiently fast with respect to the reaction rates of the decomposition and the cyclization of IHOG. Therefore, the D-aminotransferase is modified so as to efficiently produce (2R, 4R)-monatin from IHOG by provoking artificial mutation at the position involved in the efficient production of (2R, 4R)-monatin.

Examples of the methods for position-specific mutagenesis for inducing the desired mutation at a target position of the DNA may include a method using PCR (Higuchi, R., in PCR Technology 61; Erlich, H. A., Eds., Stockton Press, 1989; Carter, P., Methods in Enzymology, 154:382,1987), a method using a phage (Kramer, W. & Frits, H. J., Methods in Enzymology, 154:350,1987; Kunkel, T. A et al., Methods in Enzymology, 154:367, 1987).

Specific examples of the D-aminotransferase DNA modified so as to efficiently produce (2R, 4R)-monatin from IHOG may include DNA sequences encoding the proteins having the following amino acid sequences:

(1) Amino acid sequence having the substitution of the asparagine residue at position 100 with the alanine residue in the amino acid sequence represented by SEQ ID NO:2

(2) Amino acid sequence having the substitution of the serine residue at position 181 with the asparagine residue in the amino acid sequence represented by SEQ ID NO:2

(3) Amino acid sequence having the substitution of the alanine residue at position 182 with the lysine residue in the amino acid sequence represented by SEQ ID NO:2

(4) Amino acid sequence having the substitution of the alanine residue at position 182 with the serine residue in the amino acid sequence represented by SEQ ID NO:2

(5) Amino acid sequence having the substitution of the asparagine residue at position 183 with the serine residue in the amino acid sequence represented by SEQ ID NO:2

(6) Amino acid sequence having the substitution of the serine residue at position 243 with the glutamic acid residue in the amino acid sequence represented by SEQ ID NO:2

(7) Amino acid sequence having the substitution of the serine residue at position 243 with the leucine residue in the amino acid sequence represented by SEQ ID NO:2

(8) Amino acid sequence having the substitution of the serine residue at position 243 with the lysine residue in the amino acid sequence represented by SEQ ID NO:2

(9) Amino acid sequence having the substitution of the serine residue at position 243 with the asparagine residue in the amino acid sequence represented by SEQ ID NO:2

(10) Amino acid sequence having the substitution of the serine residue at position 243 with the glutamine residue in the amino acid sequence represented by SEQ ID NO:2

(11) Amino add sequence having the substitution of the serine residue at position 244 with the lysine residue in the amino acid sequence represented by SEQ ID NO:2

(12) Amino acid sequence having the substitution of the serine residue at position 180 with the alanine residue and the substitution of the serine residue at position 243 with the asparagine residue in the amino acid sequence represented by SEQ ID NO:2

(13) Amino acid sequence having the substitution of the serine residue at position 180 with the alanine residue and the substitution of the serine residue at position 244 with the lysine residue in the amino acid sequence represented by SEQ ID NO:2

(14) Amino acid sequence having the substitution of the serine residue at position 243 with the asparagine residue and the substitution of the serine residue at position 244 with the lysine residue in the amino acid sequence represented by SEQ ID NO:2

(15) Substitution of the asparagine residue at position 100 with the alanine residue and the substitution of the serine residue at position 181 with the alanine residue

(16) Substitution of the asparagine residue at position 100 with the alanine residue and the substitution of the alanine residue at position 182 with the serine residue

(17) Substitution of the serine residue at position 181 with the alanine residue and the substitution of the alanine residue at position 182 with the serine residue

(18) Amino acid sequence having the substitution of the asparagine residue at position 100 with the alanine residue and the substitution of the serine residue at position 243 with the asparagine residue in the amino acid sequence represented by SEQ ID NO:2

(19) Amino acid sequence having the substitution of the alanine residue at position 182 with the serine residue and the substitution of the serine residue at position 243 with the asparagine residue in the amino acid sequence represented by SEQ ID NO:2

(20) Amino acid sequence having the substitution of the serine residue at position 243 with the lysine residue in the amino acid sequence represented by SEQ ID NO:4

(21) Amino acid sequence having the substitution of the serine residue at position 243 with the asparagine residue in the amino acid sequence represented by SEQ ID NO:4

(22) Amino acid sequence having the substitution of the serine residue at position 244 with the lysine residue in the amino acid sequence represented by SEQ ID NO:4

To deduce the DNA encoding the amino acid sequence based on the above sequences (1) to (22), the universal codons for the DNA nucleotide sequences may be employed.

Examples of the DNA may also include those encoding the mutated D-aminotransferase having the amino acid sequence having the substitution, deletion, insertion, addition and/or inversion of one or several amino acid residues at the position(s) other than the positions involved in the 4R-selectivity of these mutated D-aminotransferases, i.e., other than the positions for substitution defined in (1) to (22), and having the D-aminotransferase activity capable of efficiently producing the (2R, 4R)-monatin. The definition of "one or several" is the same as that defined in the section [I] Amino acid sequence of mutated D-aminotransferase.

Examples of the DNA may also include those which hybridizes with the DNA composed of the nucleotide sequence complementary to the DNA encoding the proteins having the amino acid sequences of (1) to (22) under the stringent condition, and encodes the mutated D-aminotransferase having the D-aminotransferase activity to efficiently produce (2R, 4R)-monatin from IHOG. As used herein, the "stringent condition" refers to the condition wherein a so-called specific hybrid is formed whereas a non-specific hybrid is not formed. Although it is difficult to clearly show this condition with numeric figure, one example of the condition may be the condition wherein a pair of DNA sequences having high homology, for example, more than 85%, preferably more than 90% and particularly preferably 95% or more homology are hybridized whereas DNA sequences with lower homology than that are not hybridized (it is desirable that the homology referred to herein is the value calculated with alignment such that a number of matched bases between the compared sequences is maximized.). Another example thereof may be a washing condition of an ordinary Southern hybridization, i.e., hybridization at salt concentrations equivalent to 37° C., 0.1×SSC and 0.1% SDS, preferably 60° C., 0.1×SSC and 0.1% SDS, more preferably 65° C., 0.1× SSC and 0.1% SDS. However, as to the nucleotide sequence which hybridizes with the nucleotide sequence complementary to the nucleotide sequence described in SEQ ID NO:1 under the stringent condition, it is desirable that the resulting protein retains the D-aminotransferase activity at not less than 3%, preferably not less than 10%, more preferably not less than 30%, still more preferably not less than 50%, and further preferably not less than 70% compared to that of the protein having the amino acid sequence described in SEQ ID NO:2 under the conditions of 30° C. and pH 8.0.

Therefore, the substitution of the nucleotide may be performed at the particular position in the wild-type gene by the above site-directed mutagenesis method so as to encode these mutated D-aminotransferases.

[II-3] Production and Cultivation of Bacteria Which Produce Mutated D-aminotransferase Recombinant bacteria which express the mutated D-aminotransferase may be obtained by incorporating a DNA fragment containing the gene encoding the mutated D-aminotransferase obtained in the above into an appropriate vector and introducing into host cells.

There have been reported numerous examples for producing useful proteins such as enzymes and physiologically active substances by taking advantage of recombinant DNA technology. By the use of the recombinant DNA technology, the useful protein which is naturally present in a trace amount can be produced on a large scale. Genes to be incorporated may include the genes described in the section (ii) Preparation of mutated D-aminotransferase gene.

When the protein is produced on a large scale using the recombinant DNA technology, host cells to be transformed may include microbial cells, actinomycetal cells, yeast cells, fungal cells, plant cells and animal cells. Among them, findings on recombinant DNA operation have been accumulated as to microorganisms such as *Bacillus*, *Pseudomonas*, *Brevibacterium*, *Corynebacterium*, *Streptomyces* and *Escherichia coli*. Generally, there are numerous findings for the techniques to produce the proteins on a large scale using intestinal bacteria, and thus the intestinal bacteria, preferably *Escherichia coli* may be used.

The target aminotransferase gene may be introduced into these microorganisms using a vector such as plasmid and phage carrying the same, or the target gene may be incorporated into a chromosome in the microbial cell by homologous recombination. Preferably, a plasmid vector of multiple copy type may be used. Examples of the vector for *Escherichia coli* may include plasmids having a replication origin derived from Col E1, e.g., pUC type plasmid and pBR322 type plasmid or derivatives thereof. As a promoter for the expression of the target aminotransferase gene in these vectors, the promoter usually used for the protein production in *Escherichia coli* may be used. Examples thereof may include strong promoters such as T7 promoter, trp promoter, lac promoter, tac promoter, and PL promoter. To increase the production, it is preferable to ligate a terminator which is a transcription termination sequence to the downstream of the protein gene. This terminator may include T7 terminator, fd phage terminator, T4 terminator, terminator of tetracycline resistant gene, terminator of *Escherchia coli* trpA gene and the like. In order to select transformants, it is preferred that the vector has a marker gene such as ampicillin resistant gene. As such a plasmid, for example, expression vectors having a strong promoter such as pUC type (supplied from Takara Shuzo Co., Ltd.), pPRO type (supplied from Clontech) and pKK233-2 (supplied from Clontech) are commercially available.

The mutated D-aminotransferase of the present invention may be obtained by expressing the mutated gene which may be obtained by the direct mutation of the gene encoding the D-aminotransferase as described above. The mutated D-aminotransferase of the present invention may also be obtained by treating the D-aminotransferase-producing microorganisms (e.g., genus *Bacillus*) with ultraviolet irradiation or a mutagenic agent ordinary used for artificial mutagenesis such as N-methyl-N'-nitro-N-nitrosoguanidine (NTG), to obtain a mutant strain which produces the mutated D-aminotransferase which efficiently produces the (2R,4R) isomer from IHOG, and culturing the mutant strain.

Subsequently, the method for culturing the microorganism in the present invention will be described. As used herein, the term "microorganism" means both the culture of gene recombinant cells which expresses the mutated D-aminotransferase of the present invention and the culture of a mutant strain which has become to produce the mutated D-aminotransferase. A culturing condition described herein may be applied to both the cultivation to make the microorganism produce the mutated D-aminotransferase for obtaining the same, as well as the cultivation wherein the microorganism is cultured to produce the mutated D-aminotransferase while the reaction to produce the glutamic acid derivative is simultaneously performed.

The method for culturing the microorganism of the present invention may be performed with a medium usually used in this field, i.e., a medium containing carbon sources, nitrogen sources, inorganic salts, trace metal salts, vitamins and the like. Depending on the type of the microorganism or the culturing condition, it is also possible to promote an amino group transfer reaction activity by adding an amino compound such as an amino acid at about 0.1 to 1.0 g/dl to the medium.

When the gene recombinant cells are cultured, an agent such as ampicillin, kanamycin, neomycin, and chloramphenicol may be appropriately added corresponding to the selection marker of the vector. The expression of the recombinant gene may be increased by appropriately adding an inducer in accordance with the promoter loaded in the vector. For example, when a vector is constructed by ligating the target gene to the downstream of the lac promoter, it is possible to appropriately add isopropyl-1-thio-β-D-galactopyranoside (IPTG) at a final concentration of 0.1 mM to 5 mM. Alternatively, in place of this, it is also possible to appropriately add galactose at a final concentration of 0.1 to 5 g/dl, desirably 0.5 to 2 g/dl.

The cultivation may be performed within the range of the temperature where the microorganism used usually grows, i.e., within the range of 10 to 45° C., preferably 20 to 40° C., and more preferably 25 to 37° C. A pH value in the medium may be controlled within the range of preferably 2 to 12, more preferably 3 to 10, and still more preferably 4 to 8. An aeration condition may be set up as the condition suitable for growth of the microorganism used, and an aerobic condition is preferable. A culture period may be usually 12 to 120 hours, and preferably about 24 to 96 hours.

[B] Method for Producing (2R, 4R)-glutamic Acid Derivative Using Mutated D-aminotransferase The method for producing the optically active glutamic acid derivative of the present invention is characterized by reacting a keto acid represented by the following formula (1):

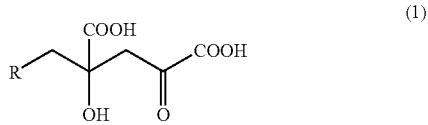

(1)

(in the general formula (1), R is an aromatic or heterocyclic ring, and the aromatic or heterocyclic ring may further have one or more substituents chosen from a halogen atom, a hydroxyl group, an alkyl group having up to 3 carbon atoms, an alkoxy group having up to 3 carbon atoms and an amino group) in the presence of the protein having the D-aminotransferase activity to act upon IHOG to produce (2R,4R)-monatin, and an amino donor, to produce a (2R,4R) isomer of a glutamic acid derivative or the salt thereof represented by the following general formula (2):

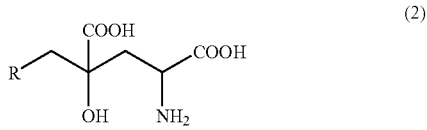

(2)

(in the general formula (2), R represents the same group as R in the general formula (1)).

[I] D-aminotransferase

In the method for producing the optically active glutamic acid derivative of the present invention, the mutated D-aminotransferase of the present invention described in the section [A] Mutated D-aminotransferase may be used as the "protein having the D-aminotransferase activity to act upon IHOG to produce (2R, 4R)-monatin".

In the method for producing the optically active glutamic acid derivative of the present invention, the (2R,4R) isomer of the glutamic acid derivative may be efficiently produced when an SR isomer of the keto acid is used as the substrate, since the reaction proceeds in the presence of the D-aminotransferase.

As used herein, "in the presence of the D-aminotransferase" means that the D-aminotransferase is present in the reaction system in which the glutamic acid derivative represented by the general formula (2) may be produced from the keto acid represented by the general formula (1). That is, the D-aminotransferase may be present in the reaction system in any form as long as the keto acid represented by the general formula (1) may be converted to the glutamic acid derivative represented by the general formula (2). For example, the D-aminotransferase alone may be added into the reaction system, or the microorganism having the relevant enzyme activity (cells or a mutant strain transformed with the recombinant DNA), the culture of the microorganism (liquid culture, solid culture, etc.), the cultured medium (from which microbial cells are removed), or the treated product of the culture may be added to the reaction system. When using the culture of the microorganism, the reaction may be performed as the microorganism is cultured, or the reaction may be performed using the culture previously prepared for obtaining the enzyme. The "treatment" herein means the treatment performed for the purpose of collecting the enzyme from the microbial cells, and may include, for example, the ultrasonic disruption, treatment with glass beads, French press and lyophilization, and the treatment with bacteriolytic enzyme, organic solvent or surfactant. Substances which have been subjected to these treatments may further be processed by standard methods (liquid chromatography, ammonium sulfate fractionation, etc.) to prepare a crude fraction of the enzyme or a purified enzyme, which may be employed as long as it has a required property.

For example, when the glutamic acid derivative is produced using the cells transformed by the recombinant DNA, the substrate may be directly added into the medium while the cells are cultured. Alternatively, the microbial cells removed from the medium or the washed microbial cells may be used. The microbial cells may be disrupted or lysed to be a treated product, which as it is may also be used. The D-aminotransferase collected from the treated microbial cells may also be used as a crude enzyme solution. Furthermore, the enzyme may be purified for use.

Moreover, the above culture or treated product may be used after entrapment in carrageenan and polyacrylamide or immobilizing it on a membrane of polyether sulfone or reproduced cellulose.

[II] Substrate Keto Acid

In the present invention, the keto acid of the general formula (1) is used as the substrate.

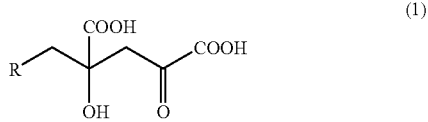

(1)

wherein R is an aromatic or heterocyclic ring, and the aromatic or heterocyclic ring may further have one or more substituents chosen from a halogen atom, a hydroxyl group, an alkyl group having up to 3 carbon atoms, an alkoxy group having up to 3 carbon atoms and an amino group.

Particularly, it is preferable that R in the formula is a phenyl or indolyl group. When R is the indolyl group, (2R, 4R)-monatin may be produced as the glutamic acid derivative of the general formula (2). When R is the phenyl group, the (2R, 4R) isomer of 4-phenylmethyl-4-hydroxy-glutamic acid (PHG) which is an analogue of monatin may be obtained as the glutamic acid derivative of the general formula (2).

The method for synthesizing the keto acid represented by the above general formula (1) is not particularly limited, and either a chemical reaction system or an enzymatic system may be used. The method for synthesizing the keto acid of the general formula (1) will be described as to the chemical reaction system and the enzymatic system in a separate manner. The method for synthesizing the keto acid of the general formula (1) is of course not limited thereto.

(II-1) Chemical Reaction System

Synthesis of the keto acid of the general formula (1) utilizing the chemical reaction system may be easily carried out through the use of the methods shown below and Reference Examples described below.

For example, the keto acid of the general formula (1) may be produced by subjecting substituted pyruvic acid represented by the following general formula (6) and oxaloacetic acid or pyruvic acid to a cross aldol reaction and a decarbonate reaction. A compound generated by the above aldol reaction is formed in the reaction system to be an important intermediate. Intentionally omitting the isolation step of the compound, the reaction may proceed to the decarbonate reaction, i.e., the subsequent step.

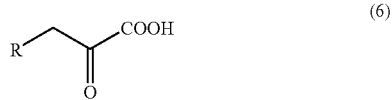

(6)

For example, when R is the indolyl group, i.e., when indole-3-pyruvic acid is used as the substituted pyruvic acid, IHOG (or a salt thereof) which is the important intermediate for producing monatin may be produced. For example, when R is the phenyl group, i.e., when phenyl pyruvic acid is used as the substituted pyruvic acid, 4-phenylmethyl-4-hydroxy-2-oxoglutaric acid (hereinbelow referred to as PHOG) (or a salt thereof) which is an intermediate keto acid corresponding to 4-phenylmethyl-4-hydroxyglutamic acid (hereinbelow referred to as PHG) which is the analogue of monatin may be produced.

There is no difficulty in determining the condition for the aldol reaction. The reaction easily proceeds only by bringing the substituted pyruvic acid and oxaloacetic acid or pyruvic acid to a reaction in an appropriate solvent in the presence of inorganic base or organic base.

Types of the solvent to be used are not particularly limited as long as the solvent is inert in the reaction.

Those skilled in the art can appropriately select a reaction temperature, an amount of the base to be used, a reaction time period and a manner of adding the starting substances in the scope where performance of the present invention is not impaired.

Example of the solvent may preferably include polar solvents such as water, methanol, acetonitrile and dimethylformamide.

Examples of the base when used may preferably include inorganic bases such as hydroxide and carbonate of alkali metals or alkali earth metals such as lithium hydroxide, sodium hydroxide, potassium hydroxide, sodium carbonate, potassium carbonate and calcium carbonate, and organic bases such as triethylamine.

The reaction temperature may preferably be about −20 to 100° C. and more preferably about 0 to 60° C.

After the aldol condensation with the substituted pyruvic acid and oxaloacetic acid as the substrates, the decarboxylation may be achieved by spontaneous decarboxylation of the condensate. However, more effective decarboxylation may be performed by adding an acid or a metal ion or both to the reaction liquid. Examples of the acid used therefor may include hydrochloric acid, sulfuric acid, phosphoric acid, acetic acid, paratoluenesulfonic acid and solid acids such as ion exchange resins. Examples of the metal ion may include transition metal ions such as nickel ion, copper ion and iron ion. The reaction temperature may preferably be about −10 to 100° C. and more preferably about 0 to 60° C.

(II-2) Enzymatic System

When the enzymatic system is employed, the substrate keto acid represented by the general formula (1) may be produced without particular difficulty by the use of an enzyme (aldolase) which catalyzes the reaction to produce the keto acid represented by the general formula (1) from the substituted pyruvic acid represented by the above general formula (6) and pyruvic acid (or oxaloacetic acid).

Examples of the microorganisms which are sources of aldolase catalyzing the above reaction may include the microorganisms belonging to the genera *Pseudomonas, Erwinia, Flavobacterium* and *Xanthomonas*.

Among the microorganisms belonging to the genera *Pseudomonas, Erwinia, Flavobacterium* and *Xanthomonas*, any microorganism may be used for the present invention as long as the microorganism produces aldolase which catalyzes the reaction to synthesize the precursor keto acid (IHOG) from indole-3-pyruvic acid and pyruvic acid (or oxaloacetic acid). However, more preferable are *Pseudomonas taetrolens* ATCC 4683, *Pseudomonas coronafaciens* AJ2791, *Pseudomonas desmolytica* AJ1582, *Erwinia* sp. AJ2917, *Xanthomonas citri* AJ2797, and *Flavobacterium rhenanum* AJ2468. Among them, particularly preferable are *Pseudomonas taetrolens* ATCC 4683 and *Pseudomonas coronafaciens* AJ2791. Particulars of the deposition of these microorganisms are shown below.

(1) *Pseudomonas coronafaciens* AJ2791 Strain
  (i) Accession number: FERM BP-8246 (transferred to the International Deposition on Nov. 22, 2002, from FERM P-18881 that had been deposited on Jun. 10, 2002)
  (ii) Date of deposit: Jun. 10, 2002
  (iii) Depositary authority: International Patent Organism Depositary, National Institute of Advanced Industrial Science and Technology (Central No.6, 1-1-1 Higashi, Tsukuba-shi, Ibaraki Prefecture, Japan)

(2) *Pseudomonas desmolytica* AJ 1582 Strain
  (i) Accession number FERM BP-8247 (transferred to the International Deposition on Nov. 22, 2002, from FERM P-18882 that had been deposited on Jun. 10, 2002)
  (ii) Date of deposit: Jun. 10, 2002
  (iii) Depositary authority: International Patent Organism Depositary, National Institute of Advanced Industrial Science and Technology (Central No.6, 1-1-1 Higashi, Tsukuba-shi, Ibaraki Prefecture, Japan)

(3) *Erwinia sp.* AJ2917 Strain
  (i) Accession number FERM BP-8245 (transferred to the International Deposition on Nov. 22, 2002, from FERM P-18880 that had been deposited on Jun. 10, 2002)
  (ii) Date of deposit: Jun. 10, 2002
  (iii) Depositary authority: International Patent Organism Depositary, National Institute of Advanced Industrial Science and Technology (Central No.6, 1-1-1 Higashi, Tsukuba-shi, Ibaraki Prefecture, Japan)

(4) *Flavobacterium rhenanum* AJ2468 Strain
  (i) Accession number FERM BP-1862
  (ii) Date of deposit: Sep. 30, 1985
  (iii) Depositary authority: International Patent Organism Depositary, National Institute of Advanced Industrial Science and Technology (Central No. 6,1-1-1 Higashi, Tsukuba-hi, Ibaraki Prefecture, Japan)

(5) *Xanthomonas citri* AJ2797 Strain
  (i) Accession number FERM BP-8250 (transferred to the International Deposition on Nov. 27, 2002 from FERM P-8462 that had been deposited on Sep. 30, 1985)
  (ii) Date of deposit: Sep. 30, 1985
  (iii) Depositary authority: International Patent Organism Depositary, National Institute of Advanced Industrial Science and Technology (Central No. 6, 1-1-1 Higashi, Tsukuba-shi, Ibaraki Prefecture, Japan)

The aldolase may be obtained by culturing the above aldolase-producing microorganism, to thereby produce and accumulate the aldolase. Alternatively, transformants which produce the aldolase may be prepared by the recombinant DNA technology, and the transformants may then be cultured to produce and accumulate the aldolase.

The reaction in the presence of the aldolase may proceed in a reaction liquid containing the aldolase, the substituted pyruvic acid represented by the general formula (6) and at least one of oxaloacetic acid and pyruvic acid, which may be adjusted to an appropriate temperature of 20 to 50° C., and left stand, shaken or stirred for 30 minutes to 5 days with keeping pH at 6 to 12.

The reaction rate may also be accelerated by adding a bivalent cation such as $Mg^{2+}$, $Mn^{2+}$, $Ni^{2+}$ and $Co^{2+}$ to the reaction liquid. In some cases, $Mg^{2+}$ is preferably used in terms of cost These bivalent cations may be added to the reaction liquid as any form of salts thereof as long as they do not inhibit the reaction, but $MgCl_2$, $MgSO_4$, $MnSO_4$ are preferably used. The concentration of these bivalent cations to be added may be determined by a simple preliminary examination by those skilled in the art, and may be in the range of 0.01 to 10 mM, preferably 0.1 to 5 mM and more preferably 0.1 to 1 mM.

An example of preferable conditions for performing the reaction may be as follows: 10% (wv) washed microbial cells of aldolase-expressing *E. coli* as an enzyme catalyst may be added to the reaction liquid composed of 100 mM buffer, 50 mM indole-3-pyruvic acid, 250 mM pyruvic acid, 1 mM $MgCl_2$ and 1% (v/v) toluene, and reaction may be performed by shaking the mixture at 33° C. for 4 hours, to thereby obtain 4-(indol-3-ylmethyl)-4-hydroxy-2-oxoglutaric acid (IHOG).

The generated keto acid of the general formula (1) may be isolated and purified by the techniques known in the art. An example of the method may be absorption of the basic amino acids by contacting the same with an ion exchange resin, which is then eluted and subsequently crystallized. Another example of the method may be discoloring and filtrating by, e.g., an active charcoal after elution, which is then followed by crystallization.

[Ill] Amino Donor

In the invention, since the D-aminotransferase is used, a D-amino acid is also used as an amino donor. The amino donor referred to herein includes amino compounds such as naturally occurring and non-naturally occurring D-amino acids. That is, D-glutamic acid, D-aspartic acid, D-alanine, D-tryptophan, D-phenylalanine, D-isoleucine, D-leucine, D-tyrosine, D-valine, D-arginine, D-asparagine, D-glutamine, D-methionine, D-ornithine, D-serine, D-cysteine, D-histidine, D-lysine and the like may be included as examples of the amino acids. The amino donor to be added to the reaction may be alone or a mixture of a plurality of donors. An inexpensive DL-amino acid may also be used.

The donor may also be supplied by adding L-amino acid or DL-amino acid into the reaction solution and making an enzyme coexist which catalyzes the reaction to racemize the amino acid, to thereby converting them into the D-amino acid as an amino donor. Preferable examples of such a racemization enzyme may include alanine racemase, glutamic acid racemase, aspartic acid racemase, and phenylalanine racemase. In this case, L-alanine, L-glutamic acid, L-phenylalanine, L-aspartic acid or a racemic mixture of any of the above L-amino acids may be added to the reaction solution during the production of the glutamic acid derivative.

[IV] Reaction Condition

In the method for producing the optically active glutamic acid derivative of the present invention, (2R, 4R) isomer of the glutamic acid derivative is efficiently produced from the substrate keto acid of the general formula (1) in the presence of the D-aminotransferase and the amino donor.

As described above, the D-aminotransferase may be added to the reaction system in any form as long as it has the enzymatic activity. For example, when the glutamic acid derivative is produced by the cells that are transformed by the recombinant DNA, the substrate keto acid and the amino donor may be added directly to the medium while culturing the cells, to constitute the reaction liquid. Alternatively, the microbial cells or the purified enzyme isolated from the medium, the substrate keto acid and the amino donor may be added to a solvent, to constitute the reaction liquid.

When microbial cells are used as a catalyst having the D-aminotransferase activity, i.e., when the cultured medium or the washed microbial cells are used, a surfactant such as Triton X and Tween or an organic solvent such as toluene and xylene may also be used in order to increase permeability of the substrate keto acid into the microbial cells. A coenzyme such as pyridoxal-5-phosphate as a reaction facilitating substance may also be added to the above medium. Specific substances for use as the ingredients of the above medium may include the following: Carbon sources are not limited as long as they are available for the microorganism to be employed, and examples thereof may include glucose, sucrose, fructose, glycerol, acetic acid and the like, and mixtures thereof. Examples of nitrogen sources to be used may include ammonium sulfate, ammonium chloride, urea, yeast extract, meat extract, corn steep liquor, hydrolyzed casein, and mixtures thereof. An example of the specific medium composition may be the medium containing 0.5 g/dl of fumaric acid, 1 g/dl of yeast extract, 1 g/dl of peptone, 0.3 g/dl of ammonium sulfate, 0.3 g/dl of $K_2HPO_4$, 0.1 g/dl of $KH_2PO_4$, 1 mg/dl of $FeSO_4 \cdot 7H_2O$ and 1 mg/dl of $MnSO_4 \cdot 4H_2O$ (pH 7.0).

When the step of the cultivation for producing the enzyme and the step of producing the glutamic acid derivative are performed separately in a sequential manner, the reaction in the step of producing the glutamic acid derivative does not have to be performed n the aerobic atmosphere. Rather the reaction may be performed under an anaerobic atmosphere. The reaction may also be performed in the system where dissolved oxygen in the reaction liquid is eliminated by nitrogen gas substitution, argon gas substitution, addition of sodium sulfite and the like.

The reaction temperature may usually be within the range where the employed enzyme has the activity, i.e., is in the range of 10 to 50° C., more preferably 20 to 40° C. and still more preferably 25 to 37° C. The pH value of the reaction solution may be adjusted into the range of usually 2 to 12, preferably 6 to 11, and more preferably 7 to 9. When the pH is high, IHOG which is the raw material of monatin may easily be decomposed spontaneously to be 3-indole-pyruvic acid and pyruvic acid, whereas when the pH is low, it is not preferable because IHOG may be easily cyclized and becomes unavailable for amination. In order to effectively inhibit the decomposition reaction and the cyclization reaction of IHOG which is the raw material of monatin, it is sometimes preferable to keep the reaction solution at pH range of 8 to 8.5. The reaction time period may be usually about 1 to 120 hours, preferably about 1 to 72 hours, and more preferably about 1 to 24 hours.

Quantification of the glutamic acid derivative or the substrate keto acid in the reaction liquid may be performed rapidly using the well-known methods. That is, a convenient method may be thin layer chromatography utilizing "Silicagel 60F254" supplied from Merck & Co., Inc. For achieving higher analysis accuracy, high performance liquid chromatography (HPLC) may be used which utilizes optical resolution columns such as "Inertsil ODS-80A" supplied from GL Sciences Inc., and "CROWNPAK CR(+)" supplied from Daicel Chemical Industries Ltd. The glutamic acid derivative accumulated in the reaction liquid may be collected from the reaction liquid by standard methods, for further use thereof. Collection of the product from the reaction liquid may be performed by well-known means usually used in the art for such a purpose. Example thereof may include operations such as filtration, centrifugation, concentration in vacuum, ion exchange chromatography, absorption chromatography and crystallization, which may be used in combination if appropriate.

The objective glutamic acid derivative may be obtained in a free form, but may also be obtained in a salt form if necessary. The salt form may be a salt with a base. Examples thereof may include inorganic bases such as sodium hydroxide, potassium hydroxide and calcium hydroxide, and organic bases such as ammonia and various amines.

EXAMPLES

The present invention will be illustrated more specifically with reference to following Examples. However, the present invention is not limited thereto.

In the following Examples, quantitative analysis of monatin and 4-phenylmethyl-4-hydroxyglutamic acid (hereinbelow abbreviated as "PHG") was performed by high performance liquid chromatography utilizing "Inertsil ODS-80A" (5 μm, 6×150 mm) supplied from GL Sciences Inc. Analysis conditions are as follows.

Mobile phase: aqueous solution of 12% (vN) acetonitrile/0.05% (v/v) trifluoroacetic acid Flow rate: 1.5 mL/min Column temperature: 30° C.

Detection: UV 210 nm

In accordance with the above conditions, (2S, 4S)-monatin and (2R, 4R)-monatin are eluted at the retention time of 12.1 minutes, (2S, 4R)-monatin and (2R, 4S)-monatin are at 9.7 minutes, (2S, 4S)-PHG and (2R, 4R)-PHG are at 7.2 minutes, and (2S, 4R)-PHG and (2R, 4S)-PHG are at 6.0 min.

When needed, the analysis by high performance liquid chromatography utilizing an optical resolution column, "CROWNPAK CR(+)" (4.6×150 mm) supplied from Daicel Chemical Industries Ltd. was also performed. The analysis conditions are as follows.

(Analysis of Monatin)

Mobile phase: aqueous solution of perchloric acid (pH 1.5)/10% (v/v) methanol

Flow rate: 0.5 mL/min

Column temperature: 30° C.

Detection: UV210 nm

In accordance with the above conditions, optical isomers of monatin can be eluted in the order of (2R, 4S), (2R, 4R), (2S, 4R) and (2S, 4S) at the retention time of 42, 57, 64 and 125 minutes, respectively.

(Analysis of PHG)

Mobile phase: aqueous solution of perchloric acid (pH 1.5)

Flow rate: 1 mL/min

Column temperature: 30° C.

Detection: UV 210 nm

In accordance with the above conditions, optical isomers of PHG can be eluted in the order of (2R, 4S), (2R, 4R), (2S, 4R) and (2S, 4S) at the retention time of 20, 28, 31 and 46 minutes, respectively.

Example 1

Screening for Microorganisms Having D-aminotransferase Activity for PHOG Amination Microbial strains to be tested were inoculated on bouillon agar plate (Eiken Chemical Co., Ltd.), and cultured at 30° C. for 24 hours. The cells were then inoculated at about 5% (w/v) into 1 ml of a reaction liquid composed of 100 mM Tris-HCl (pH 7.6), 50 mM PHOG, 100 mM D-glutamic acid, 100 mM D-alanine, 1 mM pyridoxal-5'-phosphate and 0.5% (v/v) toluene. The reaction liquid was then incubated at 30° C. for 16 hours. After the completion of the reaction, produced PHG was analyzed. As a result, the 2R-PHG producing activity from PHOG was found in the microorganisms shown in Table 2. Thus (2R, 4S)-PHG and (2R, 4R)-PHG were produced from PHOG.

TABLE 2

| Strains | PHG generation (mM) | |
| --- | --- | --- |
| | (2R,4R) | (2R,4S) |
| Bacillus macerans AJ1617* | 7.1 | 7.0 |
| Bacillus sphaericus ATCC 10208 | 16.6 | 16.5 |
| Bacillus pulvifaciens AJ1327 | 2.8 | 2.6 |
| Paenibacillus larvae subsp. pulvifaciens ATCC 13537 | 3.0 | 2.8 |
| Paenibacillus macerans ATCC 8244 | 6.5 | 6.5 |
| Bacillus lentus AJ12699 | 4.6 | 4.6 |
| Bacillus lentus ATCC 10840 | 4.2 | 4.3 |

*FERM BP-8243

Example 2

Cloning of Dat Gene (Bmdat) Derived From *Bacillus macerans* AJ1617 Strain and Construction of Expression-Plasmid (1) Preparation of Chromosomal DNA

*Bacillus macerans* AJ 1617 strain was cultured using 50 mL of bouillon medium at 30° C. overnight (preculture). 5 mL of this cultured medium was inoculated into a main culture consisting 50 mL of bouillon medium. After culturing until a logarithmic growth late phase, 50 mL of the cultured broth was centrifuged (12000×g, 4° C., 15 min.) to harvest cells. From thus obtained cells, chromosomal DNA was prepared in accordance with standard methods.

(2) Isolation of Bmdat Gene From a Genomic Library

1 U of a restriction enzyme EcoRI was added to 30 μg of chromosomal DNA derived from *Bacillus macerans* AJ1617, and incubated at 37° C. for 3 hours to perform partial digestion. Subsequently, fragments of 3 to 6 kbp were collected from this partially digested DNA by agarose gel electrophoresis. These DNA fragments were ligated to 1 μg of EcoRI-digested fragment of plasmid pUC118 (already treated with BAP, supplied from Takara Shuzo Co., Ltd.), and *E. coli* JM109 was transformed therewith to prepare a genomic library. Thus transformed cells of *E. coli* were plated in LB medium (1% tryptone, 0.5% yeast extract, 1% sodium chloride, 2% agar, pH 7.0) containing 0.1 mg/mL of ampicillin. Each colony appeared was inoculated into 1 mL of the LB liquid medium containing 0.1 mg/mL of ampicillin and 0.1 mM isobutyl-1-thio-β-D-galactopyranoside (IPTG). The liquid medium was then cultured at 37° C. overnight. 200 to 400 μL of the cultured medium were centrifuged to harvest the cells. The harvested cells were then washed. The cells thus obtained were resuspended into 200 μL of a reaction liquid containing 100 mM Tris-HCl (pH 8.0), 50 mM sodium pyruvate, 100 mM D-glutamic acid, 1 mM pyridoxal-5'-phosphate and 1% (v/v) toluene. The reaction liquid was incubated at 30° C. for 30 min, and then centrifuged. Five microliter of the obtained supernatant was added to a 96-well microtiter plate in which each well contains 200 μL of a solution for quantitative analysis for pyruvate. The solution contained 100 mM Tris-HCl (pH 7.6), 1.5 mM NADH, 5 mM $MgCl_2$, 16 U/mL lactate dehydrogenase (supplied from Oriental Yeast Co., Ltd.). After incubation at 30° C. for 10 minutes, absorbance of the reaction solution at 340 nm was measured using a plate reader (Spectra Max 190, supplied from Molecular device). The same reaction was performed with addition of sodium pyruvate at final concentrations varying from 0.2 to 1 mM. Using them as standards, decreased amounts of pyruvic acid in the above reaction solution were quantitatively analyzed, to detect the D-aminotransferase activity (DAT).

Through the above screening procedure for the clones with the DAT activity, the transformant exhibiting the DAT activity was obtained. The plasmid containing the D-aminotransferase gene was prepared from this transformant, and designated as pUCBMDAT. The plasmid pUCBMDAT was digested with EcoRI and subjected to agarose gel electrophoresis. Consequently, the length of the inserted fragment was estimated to be about 3.3 kbp.

(3) Nucleotide Sequence of Inserted Fragment

The nucleotide sequence of inserted fragment of the plasmid pUCBMDAT was determined by a dideoxy method. As a result, an ORF composed of about 850 bps corresponding to the sequence of 630th to 1481st in the SEQ ID NO: 1 was found. A homology search showed that the ORF exhibited 91% homology in terms of amino acid sequence with the D-aminotransferase gene derived from *Bacillus sphaericus* ATCC 10208, 66% homology in terms of amino acid sequence with the D-aminotransferase gene derived from *Bacillus* sp. YM-1 strain, and 42% homology in terms of amino acid sequence with the D-aminotransferase gene derived from *Bacillus licheniformis* ATCC 10716. The homology referred to herein is a value calculated with the gene analysis software "genetyx ver. 6" (Genetyx) with default parameters. From these results, it has been found out that this ORF encodes a D-aminotransferase gene.

Example 3

Conversion of IHOG to 2R-monatin and Conversion of PHOG to 2R-PHG Using *E. coli* Expressing D-aminotransferase Derived From *Bacillus macerans* (BMDAT)

(1) Preparation of BMDAT-Expressing *E. coli*

*E. coli* transformants with pUCBMDAT were inoculated to 3 mL of LB medium (1 g/dL of bacto tryptone, 0.5 g/dL of yeast extract and 1 g/dL of NaCl) containing 0.1 mg/mL of ampicillin and 0.1 mM isopropyl-1-thio-β-D-galactopyranoside (IPTG). The medium was then cultured with shaking at 37° C. for 16 hours. Cells were collected from the cultured medium and washed to prepare cells of the BMDAT-expressing *E. coli*.

(2) Reaction With Washed Microbial Cells of BMDAT-Expressing *E. coli*

The microbial cells prepared in (1) above were suspended at 2% (w/v) in 1 mL of a reaction liquid composed of 100 mM Tris-HCl (pH 8.0), 50 mM IHOG, 200 mM D-alanine, 1 mM pyridoxal-5'-phosphate and 0.5% (v/v) toluene. The suspension was then incubated with shaking at 33° C. for 16 hours, and the amount of 2R-monatin thus produced was determined. As a result, 16.4 mM of (2R, 4S)-monatin and 17.0 mM of (2R, 4R)-monatin were produced.

The reaction was also performed in a reaction liquid composed of 100 mM Tris-HCl (pH 8.0), 50 mM PHOG, 200 mM D-alanine, 1 mM pyridoxal-5'-phosphate and 0.5% (v/v) toluene. The amount of 2R-PHG thus produced after the incubation was determined. As a result, 17.1 mM of (2R, 4S)-PHG and 19.2 mM of (2R, 4R)-PHG were produced.

Example 4

Preparation of Mutated BMDATs (1) Construction of Mutated Plasmids

For construction of mutated BMDAT-expressing plasmids by site-directed mutagenesis, QuikChange Site-directed Mutagenesis Kit supplied from Stratagene was used. First, oligo DNA primers (two in a pair) were synthesized. These primers were designed to introduce a target nucleotide substitution and to be complementary to each strand of double stranded DNA. The name of mutated enzymes prepared thereby and the sequences of the synthetic oligo DNA primers used for site-directed mutagenesis are listed in Table 3.

Each name of the mutated enzyme consists of "an amino acid residue in the wild-type enzyme, a residue number, and a substituted amino acid residue" in this order. For example, S243N mutated enzyme means that a Ser (S) residue at position 243 of the wild-type enzyme was substituted with an Asn (N) residue.

TABLE 3

| Plasmid | Primer | Sequence |
|---|---|---|
| pS180A | S180A-S | GAT ATC GTG ACA GAA TGC GCT TCA GCT AAT GTT TAC GG (38mer, SEQ ID: 5) |
|  | S180A-AS | CCG TAA ACA TTA GCT GAA GCG CAT TCT GTC ACG ATA TC (38mer, SEQ ID: 6) |
| pS181D | S181D-S | GAT ATC GTG ACA GAA TGC TCT GAC GCT AAT GTT TAC GG (38mer, SEQ ID: 7) |
|  | S181D-AS | CCG TAA ACA TTA GCG TCA GAG CAT TCT GTC ACG ATA TC (38mer, SEQ ID: 8) |
| pA182K | A182K-S | CAG AAT GCT CTT CAA AGA ATG TTT ACG GAA TTA AAG (36mer, SEQ ID: 9) |
|  | A182K-AS | CTT TAA TTC CGT AAA CAT TCT TTG AAG AGC ATT CTG (36mer, SEQ ID: 10) |
| pN183S | N183S-S | GTG ACA GAA TGC TCT TCA GCT AGT GTT TAC GGA ATT AAA G (40mer, SEQ ID: 11) |
|  | N183S-AS | CTT TAA TTC CGT AAA CAC TAG CTG AAG AGC ATT CTG TCA C (40mer, SEQ ID: 12) |
| pS243E | S243E-S | GAA ATC ATT GTG TCG TCT GTA GAG TCT GAG GTT ACG (36mer, SEQ ID: 13) |
|  | S243E-AS | CGT AAC CTC AGA CTC TAC AGA CGA CAC AAT GAT TTC (36mer, SEQ ID: 14) |
| pS243L | S243L-S | GAA ATC ATT GTG TCG TCT GTA TTG TCT GAG GTT ACG (36mer, SEQ ID: 15) |
|  | S243L-AS | CGT AAC CTC AGA CAA TAC AGA CGA CAC AAT GAT TTC (36mer, SEQ ID: 16) |
| pS243K | S243K-S | GAT GAA ATC ATT GTG TCG TCT GTA AAA TCT GAG GTT ACG CCA GTC (45mer, SEQ ID: 17) |
|  | S243K-AS | GAC TGG CGT AAC CTC AGA TTT TAC AGA CGA CAC AAT GAT TTC ATC (45mer, SEQ ID: 18) |
| pS243N | S243N-S | GAA ATC ATT GTG TCG TCT GTA AAT TCT GAG GTT ACG CCA G (40mer, SEQ ID: 19) |
|  | S243N-AS | CTG GCG TAA CCT CAG AAT TTA CAG ACG ACA CAA TGA TTT C (40mer, SEQ ID: 20) |
| pS243Q | S243Q-S | GAA ATC ATT GTG TCG TCT GTA CAG TCT GAG GTT ACG CCA G (40mer, SEQ ID: 21) |
|  | S243Q-AS | CTG GCG TAA CCT CAG ACT GTA CAG ACG ACA CAA TGA TTT C (40mer, SEQ ID: 22) |
| pS244K | S244K-S | CAT TGT GTC GTC TGT ATC TAA AGA GGT TAC GCC AGT CAT TG (41mer, SEQ ID: 23) |
|  | S244K-AS | CAA TGA CTG GCG TAA CCT CTT TAG ATA CAG ACG ACA CAA TG (41mer, SEQ ID: 24) |
| pS243N/ S244K | S243NS244K-S | GAA ATC ATT GTG TCG TCT GTA AAT AAA GAG GTT ACG CCA G (40mer, SEQ ID: 25) |
|  | S243NS244K-AS | CTG GCG TAA CCT CTT TAT TTA CAG ACG ACA CAA TGA TTT C (40mer, SEQ ID: 26) |

According to the manufacture's instructions, the mutated plasmids were constructed using the wild-type BMDAT-expressing plasmid pUCBMDAT prepared in Example 2 as a template. For example, upon construction of pS243N, pUCBMDAT as the template and primers S243N-S and S243N-AS were used, and the mutated BMDAT-expressing plasmid was amplified under the following conditions: (95° C. for 30 sec., 56° C. for one min. and 68° C. for 8 min.)×18 cycles.

The template pUCBMDAT was digested by the treatment with a restriction enzyme DpnI which recognizes and cleaves methylated DNA. With the resulting reaction liquid, *E. coli* JM109 was transformed. The plasmid was prepared from the transformant, and the nucleotide sequence thereof was determined to confirm that the intended nucleotide substitution had been introduced.

Double-mutated enzyme-expressing plasmid was made in the same way as the above using one mutated gene-expressing plasmid as the template. Specifically, pS243N/S180A was prepared using pS243N as a template, and primers S180A-S and S180A-AS. pS244K/S180A was prepared using pS244K as a template, and primers S180A-S and S180A-AS. pS243N/S244K was prepared using pS244K as a template, and primers S243NS244K-S and S243NS244K-AS.

(2) Preparation of Mutated BMDAT-Expressing *E. coli*

*E. coli* transformants containing each plasmid with mutated BMDAT gene or pUCBMDAT were inoculated to 3 mL of LB medium (1 g/dL of bacto tryptone, 0.5 g/dL of yeast extract and 1 g/dL of NaCl) containing 0.1 mg/mL of ampicillin and 0.1 mM isopropyl-1-thio-β-D-galactopyranoside (IPTG). The medium was then cultured with shaking at 37° C. for 16 hours. Cells were harvested from the cultured medium and washed Expression of each mutated BMDAT was confirmed with SDS-PAGE. Cells harvested form 250 µL of the cultured broth were resuspended in 500 µL of an SDS-PAGE sample buffer and boiled for 10 minutes for cell lysis and denaturation. 5 to 10 µL of the supernatant obtained by centrifugation (10,000×g, 10 min.) was subjected to SDS-PAGE. As a result, bands which specifically appeared at a position around 32 kDa were observed in all strains to which the wild-type- and mutated BMDAT-expressing plasmids had been introduced, whereby the expression of the wild-type and mutated BMDAT was confirmed.

Example 5

Conversion of IHOG to 2R-monatin and Conversion of PHOG to 2R-PHG Using Mutated BMDAT-Expressing E. coli Using a series of mutated BMDAT-expressing E. coli strains prepared in Example 4 as a catalyst, 2R-monatin was produced from 4R, S-IHOG, and 2R-PHG was produced from 4R, S-PHOG. The microbial cells collected by centrifuging 400 µL of the cultured medium were suspended in a reaction solution having the following composition.

Reaction solution of IHOG: 100 mM Tris-HCl (pH 8.0), 50 mM 4R, S-IHOG, 200 mM D-alanine, 1 mM pyridoxal-5'-phosphate and 0.5% (v/v) toluene Reaction solution of PHOG: 100 mM Tris-HCl (pH 8.0), 50 mM 4R, S-PHOG, 200 mM D-alanine, 1 mM pyridoxal-5'-phosphate and 0.5% (v/v) toluene The suspension was incubated at 30° C. for 16 hours, and then the amount of 2R-monatin and 2R-PHG thus produced were determined. The results are shown in Table 4.

TABLE 4

| Plasmid | Amination reaction of PHOG | | | Amination reaction of IHOG | | |
| --- | --- | --- | --- | --- | --- | --- |
| | 2R,4S-PHG (mM) | 2R,4R-PHG (mM) | 4R selectivity (%) | 2R,4S-monatin (mM) | 2R,4R-monatin (mM) | 4R selectivity (%) |
| pS180A | 17.3 | 19.3 | 53 | 15.3 | 17.4 | 53 |
| pS181D | 0.0 | 1.3 | 100 | 0.0 | 2.4 | 100 |
| pA182K | 5.1 | 18.2 | 78 | 4.3 | 6.7 | 60 |
| pN183S | 4.3 | 7.2 | 62 | 4.9 | 7.3 | 60 |
| pS243E | 0.0 | 2.9 | 100 | 0.2 | 3.7 | 95 |
| pS243L | 0.0 | 1.4 | 100 | 0.2 | 3.9 | 95 |
| pS243K | 3.5 | 7.3 | 68 | 5.0 | 11.9 | 70 |
| pS243N | 2.8 | 18.6 | 87 | 1.0 | 12.9 | 93 |
| pS243Q | 2.0 | 10.2 | 84 | 1.1 | 6.4 | 85 |
| pS244K | 5.0 | 22.0 | 81 | 5.5 | 12.0 | 69 |
| pS243N/S180A | 3.4 | 17.1 | 83 | 1.9 | 17.5 | 90 |
| pS244K/S180A | 5.3 | 20.2 | 79 | 6.6 | 15.0 | 69 |
| pS243N/S244K | 0.5 | 19.6 | 97 | 0.2 | 11.0 | 98 |
| pUCBMDAT | 17.1 | 19.2 | 53 | 16.4 | 17.0 | 51 |
| pUC18 | 0.0 | 0.0 | — | 0.0 | 0.0 | — |

As a result, it was found out that 4R-selectivity was enhanced as to the mutated BMDAT in which the mutation had been introduced at S181, A182, N183, S243 and S244. The 4R-selectivity referred to herein is a ratio of the (2R, 4R) isomer out of the total 2R-PHG or 2R-monatin product. Particularly with S243N, 12.9 mM (2R, 4R)-monatin and 1.0 mM (2R, 4S)-monatin were produced, and the 4R-selectivity was thus enhanced to 93%. With S244K, 12.0 mM (2R, 4R)-monafin and 5.5 mM (2R, 4S)-monatin were produced, and the 4R-selectivity was thus enhanced to 69%.

Double-mutated enzymes in which the mutant S180A was further introduced to these mutated DAT were prepared. With S243N/S180A, 17.5 mM (2R,4R)-monatin and 1.9 mM (2R, 4S)-monatin were produced (4R-selectivity: 90%). Although the 4R-selectivity was slightly reduced, the amount of the (2R, 4R)-monatin thus produced increased in comparison with that in S243N. With S244K/S180A, 15.0 mM (2R, 4R)-monatin and 6.6 mM (2R, 4S)-monatin were produced (4R-selectivity: 79%). The amount of (2R, 4R)-monabn thus produced increased in comparison with that in S244K. That is, it has been found out that introduction of the mutation S180A into the mutated BMDAT having an enhanced 4R-selectivity results in further increase in the amount of (2R, 4R)-monatin production.

An enzyme having double mutation S243N/S244K was also examined. Consequently, 11.0 mM (2R, 4R)-monatin and 0.2 mM (2R, 4S)-monatin were produced, and the 4R-selectivity was thus enhanced up to 98%.

Example 6

Production of E coli. Expressing D-Transaminase Derived From Bacillus sphaericus (BSDAT) and Production of 2R-monatin by Reaction of Washed Microbial Cells (1) Construction of Expression Plasmid In order to express the D-transaminase gene derived from Bacillus sphaericus (hereinbelow abbreviated as "bsdat") in E. coli, plasmid pUCBSDAT in which the bsdat gene was ligated to the downstream of lac promoter of pUC18 was constructed as follows. First, using chromosomal DNA of Bacillus sphaericus ATCC 10208 strain as a template and using oligonucleotides shown in the following Table 5 as primers, the gene was amplified by PCR. This amplifies a DNA fragment corresponding to the sequence of 8th to 1275th in the dat nucleotide sequence described in SEQ ID NO:2 in the text of European Patent Publication EP 0736604. This fragment was treated with BamHI and PstI, ligated to pUC18 that had been digested with BamHI and PstI, and then introduced into E. coli JM109. A strain containing the objective plasmid was selected among ampicillin resistant strains to thereby construct the expression plasmid, pUCBSDAT.

TABLE 5

Sequences of primers for BSDAT cloning

SEQ ID NO: 27   5'-CCG GGA TTC GTT AAT CCA AAC GTT AGC TG

SEQ ID NO: 28   5'-GGC CTG CAG TTA GGC ATT AAT TGA AAT TGG (2) Preparation of *E. coli* Expressing BSDAT

*E. coli* transformants containing pUCBSDAT were cultivated in the LB medium (1 g/dL of bacto tryptone, 0.5 g/dL of yeast extract and 1 g/dL of NaCl) containing 0.1 mg/mL of ampicillin at 37° C. for 16 hours. Subsequently, 1 mL of thus obtained broth was added to a 500 mL Sakaguchi flask in which contains 50 mL of the LB medium, and main cultivation was performed at 37° C. After 2.5 hours of cultivation, isopropyl-1-thio-β-D-galactopyranoside (IPTG) was added thereto at a final concentration of 1 mM, and the cultivation was performed for additional 4 hours. Cells were harvested from the cultured medium and washed to prepare the cells of BSDAT-expressing *E. coli*.

(3) Reaction With Washed Microbial Cells of BSDAT-Expressing *E. coli*

The microbial cells prepared in the above (2) were suspended at 5% (w/v) in 1 mL of a reaction liquid composed of 100 mM Tris-HCl (pH 7.6), 50 mM IHOG, 200 mM D-alanine, 1 mM pyridoxal-5'-phosphate and 0.5% (v/v) toluene. One ml of the suspension was then transferred to a 10 mL test tube, and incubated with shaking at 30° C. for 18 hours. After the incubation, the amount of 2R-monatin thus produced was determined. As a result, 13.8 mM (2R, 4R)-monatin and 12.7 mM (2R, 4S)-monatin were produced from IHOG.

Example 7

Preparation of Mutated BSDAT (1) Construction of Mutated Plasmids

For constructing the mutated BSDAT-expressing plasmids by site-directed mutagenesis, QuikChange Site-directed Mutagenesis Kit supplied from Stratagene was used. First, oligo DNA primers (two in a pair) were synthesized. These primers were designed to introduce target nucleotide substitution and to be complementary to each strand of double stranded DNA. The names of mutated enzymes prepared thereby and the sequences of the synthetic oligo DNA primers used for introducing mutations are shown in Table 6. Each name of the mutated enzyme consists of "an amino acid residue in the wild-type enzyme, a residue number, and a substituted amino acid residue" in this order. For example, S243N mutated enzyme means that a Ser (S) residue at position 243 of the wild-type enzyme was substituted with an Asn (N) residue.

TABLE 6

Sequences of primers for site-directed mutagenesis of BSDAT

| Plasmid | Primer | Sequence |
|---------|--------|----------|
| pBS-S243K | BS-S243K-S | GAA ATT ATT GTG TCT TCT GTT AAA TCT GAA GTG ACA CCG (39mer, SEQ ID: 29) |
|  | BS-S243K-AS | CGG TGT CAC TTC AGA TTT AAC AGA AGA CAC AAT AAT TTC (39mer, SEQ ID: 30) |
| pBS-S243N | BS-S243N-S | GAA ATT ATT GTG TCT TCT GTT AAC TCT GAA GTG ACA CCG (39mer, SEQ ID: 31) |
|  | BS-S243N-AS | CGG TGT CAC TTC AGA GTT AAC AGA AGA CAC AAT AAT TTC (39mer, SEQ ID: 32) |
| pBS-S244K | BS-S244K-S | GTG TCT TCT GTT TCA AAA GAA GTG ACA CCG GTT ATC (36mer, SEQ ID: 33) |
|  | BS-S244K-AS | GAT AAC CGG TGT CAC TTC TTT TGA AAC AGA AGA CAC (36mer, SEQ ID: 34) |

According to the manufacturer's instructions, the mutated plasmids were constructed using the wild-type type BSDAT-expressing plasmid pUCBSDAT prepared in Example 6 as a template. For example, upon producing pBS-S243N, pUCBSDAT as the template and primers BS-S243N-S and BS-S243N-AS were used, and the mutated BSDAT-expressing plasmids were amplified under the following conditions: (95° C. for 30 sec., 55° C. for one min. and 68° C. for 8 min.)×18 cycles.

The template pUCBSDAT was digested by a restriction enzyme DpnI which recognizes and cleaves methylated DNA. With the resulting reaction liquid, *E. coli* JM109 was transformed. The plasmids were prepared from the transformant, and the nucleotide sequence thereof was determined to confirm that the intended nucleotide substitution had been introduced.

(2) Production of *E. coli* Expressing Mutated BSDAT

*E. coli* transformants containing each plasmid with mutated BSDAT gene or pUCBSDAT were inoculated to 3 mL of LB medium (1 g/dL of bacto tryptone, 0.5 g/dL of yeast extract and 1 g/dL of NaCl) containing 0.1 mg/mL of ampicillin and 0.1 mM isopropyl-1-thio-β-D-galactopyranoside (IPTG). The medium was then cultured with shaking at 37° C. for 16 hours. Cells were collected from the cultured medium and washed to prepare the BSDAT-expressing *E. coli*. Expression of each mutated BSDAT was confirmed by SDS-PAGE. The cells harvested from 250 μL of the cultured medium were resuspended in 500 μL of an SDS-PAGE sample buffer and boiled for 10 minutes for cell lysis and denaturation, and 5 to 10 μL of the supernatant obtained by centrifugation (10,000× g, 10 min.) was subjected to SDS-PAGE. As a result, bands which specifically appeared at a position around 32 kDa were observed in all strains to which the wild-type- and mutated BSDAT-expressing plasmids had been introduced, whereby the expression of the wild-type and mutated BSDAT were confirmed.

Example 8

Conversion of IHOG to 2R-monatin Using Mutated BSDAT-Expressing *E. coli*

Using a series of mutated BSDAT-expressing *E. coli* strains prepared in Example 7, 2R-monatin was produced from 4R, S-IHOG. The microbial cells prepared by centrifuging 400 μL of the cultured medium were suspended in the reaction solution having the following composition.

Reaction solution of IHOG: 100 mM Tris-HCl (pH 8.0), 50 mM 4R, S-IHOG, 200 mM D-alanine, 1 mM pyridoxal-5'-phosphate and 0.5% (v/v) toluene The suspension was incubated at 30° C. for 16 hours, and then the amount of 2R-monatin thus produced was analyzed. The results are shown in Table 7.

TABLE 7

Amount of produced 2R-monatin with mutated BSDAT

| Plasmid | IHOG amination reaction | | |
|---|---|---|---|
| | 2R,4S-monatin (mM) | 2R,4R-monatin (mM) | 4R selectivity (%) |
| pBS-S243K | 3.7 | 7.4 | 67 |
| pBS-S243N | 1.0 | 9.9 | 92 |
| pBS-S244K | 6.1 | 12.7 | 68 |
| PUCBSDAT | 12.7 | 13.8 | 52 |
| pUC18 | 0.0 | 0.0 | — |

As a result, it was found out that the 4R-selectivity was enhanced as to the mutated BSDAT in which the mutation had been introduced at S243 and S244. The 4R-selectivity referred to herein is a ratio of the (2R, 4R) isomer out of the total 2R-monatin product Particularly with S243N, 9.9 mM (2R, 4R)-monatin and 1.0 mM (2R, 4S)-monatin were produced, and the 4R-selectivity was thus enhanced to 92%. With S244K, 12.7 mM (2R, 4R)-monatin and 6.1 mM (2R, 4S)-monatin were produced, and the 4R-selectivity was thus enhanced to 68%.

From these results, it has been found out that it is possible to improve the 4R-selectivity of DATs which have homology with BMDAT(as an example, BSDAT), by introducing the mutation at a certain position which corresponds to a position in BMDAT, introduction of mutation at which in BMDAT also results in selective production of 4R-isomer of monatin (as examples, S243, S244).

Example 9

Construction of Mutated BMDAT

The mutated BMDAT-expressing plasmid was prepared in the same way as that in Example 4 to prepare BMDAT-expressing *E. coli*. The sequences of synthetic oligo DNA primers used for introducing the mutation are shown in Table 8.

TABLE 8

Sequences of primers for site-directed mutagenesis of BMDAT

| Plasmid | Primer | Sequence |
|---|---|---|
| pN100A | N100A-S | GGG GCT AAT TCA CGT GCT CAC GTT TTC CCG GAT GC (35MER, SEQ ID: 35) |
| | N100A-AS | GCA TCC GGG AAA ACG TGA GCA CGT GAA TTA GCC CC (35MER, SEQ ID: 36) |
| pS181A | S181A-S | GTG ACA GAA TGC TCT GCA GCT AAT GTT TAC GG (32MER, SEQ ID: 37) |
| | S181A-AS | CCG TAA ACA TTA GCT GCA GAG CAT TCT GTC AC (32MER, SEQ ID: 38) |
| pA182S | A182S-S | GTG ACA GAA TGC TCT TCA TCT AAT GTT TAC GGA ATT AAA G (40MER, SEQ ID: 39) |
| | A182S-AS | CTT TAA TTC CGT AAA CAT TAG ATG AAG AGC ATT CTG TCA C (40MER, SEQ ID: 40) |
| pS181A/A182S | S181A/A182S-S | GAT ATC GTG ACA GAA TGC TCT GCA TCT AAT GTT TAC GG (38MER, SEQ ID: 41) |
| | S181A/A182S-AS | CCG TAA ACA TTA GAT GCA GAG CAT TCT GTC ACG ATA TC (38MER, SEQ ID: 42) |

Example 10

Conversion of IHOG to 2R-monatin and Conversion of PHOG to 2R-PHG by Mutated BMDAT-Expressing *E. coli*

Using a series of mutated BMDAT-expressing *E. coli* strains prepared in Example 9, 2R-monatin was produced from 4R, S-IHOG, and 2R-PHG was produced from 4R, S-PHOG. The microbial cells prepared by centrifuging 400 μL of the cultured medium were suspended in a reaction solution having the following composition.

Reaction solution of IHOG: 100 mM Tris-HCl (pH 8.0), 100 mM 4R, S-IHOG, 400 mM D-alanine, 1 mM pyridoxal-5'-phosphate and 0.5% (v/v) toluene Reaction solution of PHOG: 100 mM Tris-HCl (pH 8.0), 100 mM 4R, S-PHOG, 400 mM D-alanine, 1 mM pyridoxal-5'-phosphate and 0.5% (v/v) toluene The suspension was incubated at 30° C. for 16 hours, and then the amount of 2R-monatin and 2R-PHG thus produced were analyzed. The results are shown in Table 9.

As a result, it was found out that the amount of (2R, 4R)-monatin thus produced increased as to the mutated BMDAT of A182S, S243N/N100A, S243N/A182S, N100A/S181A and N100A/A182S in comparison with that in the wild-type enzyme. Particularly, as to the mutated BMDAT of S243N/N100A and S243N/A182S, it was found out that the amount of (2R, 4R)-monatin thus produced increased while the 4R-selectivity was kept at 80% or more.

TABLE 9

| Plasmid | PHOG amination reaction | | | IHOG amination reaction | | |
|---|---|---|---|---|---|---|
| | 2R,4S-PHG (mM) | 2R,4R-PHG (mM) | 4R selectivity (%) | 2R,4S-Monatin (mM) | 2R,4R-monatin (mM) | 4R selectivity (%) |
| pA182S | 39.3 | 42.3 | 52 | 27.5 | 30.6 | 53 |
| pS243N/N100A | 3.7 | 32.3 | 90 | 5.0 | 27.4 | 84 |
| pS243N/A182S | 5.5 | 40.9 | 88 | 7.5 | 30.0 | 80 |
| pN100A/S181A | 42.8 | 47.8 | 53 | 21.9 | 28.6 | 57 |
| pN100A/A182S | 33.6 | 36.4 | 52 | 24.7 | 29.7 | 55 |
| pUCBMDAT | 34.9 | 34.2 | 49 | 18.3 | 19.1 | 51 |

Example 11

Measurement of Amination Reaction Rate With Mutated BMDATs

*E. coli* transformants containing each plasmid with mutated BMDAT gene or pUCBMDAT were inoculated to 3 mL of casamino acid medium (0.5 g/dL of ammonium sulfate, 0.14 g/dL of $KH_2PO_4$, 0.23 g/dL of citrate $2Na \cdot 3H_2O$, 0.1 g/dL of $MgSO_4 \cdot 7H_2O$, 2 mg/dL of $FeSO_4$, 2 mg/dL of $MnSO_4$, 2 mg/dL of pyridoxine hydrochloride, 0.1 mg/dL of thiamine, 1 g/dL of casamino acid, 0.3 g/dL of glycerol, pH 7.5) containing 0.1 mg/mL of ampicillin and 0.1 mM IPTG. The medium was then cultured with shaking at 37° C. for 16 hours. Cells were collected from 1 mL of the cultured medium, washed, suspended in 1 mL of 20 mM Tris-HCl (pH 7.6), and ultrasonically disrupted at 4° C. for 30 min. The sonicates were centrifuged at 15,000 rpm for 5 minutes, and the supernatant thereof was used as an enzyme catalyst For the measurement of the D-aminotransferase activity (hereinbelow referred to as DAT activity), the transamination activity with D-alanine as the amino donor to α-ketoglutaric acid was enzymatically measured by analyzing pyruvic acid produced from D-alanine as the reaction proceeds. The results are shown in Table 10.

Reaction conditions: 100 mM Tris-HCl (pH 8.0), 0.2 mM NADH, 0.1 mM pyridoxal-5'-phosphate 5 U/mL lactate dehydrogenase, 10 mM D-alanine, 10 mM α-ketoglutaric acid, 30° C. A reduction of absorbance at 340 nm was measured.

As a result, it was found out that the DAT activity increased in the mutated BMDAT of N100A, S181A, A182S, N100A/S181A, N100A/S182S, S181A/A182S, S243N/N100A and S243N/A182S compared to the wild-type enzyme.

TABLE 10

DAT activity of mutated BMDAT

| Plasmid | DAT activity (U/mg) |
|---|---|
| pN100A | 9.9 |
| pS181A | 10.2 |
| pA182S | 10.4 |
| pN100A/S181A | 13.0 |
| pN100A/A182S | 14.8 |
| pS181A/A182S | 12.2 |
| pS243N/N100A | 10.0 |
| pS243N/S180A | 3.7 |
| pS243N/A182S | 10.7 |
| PUCBMDAT | 6.3 |

Example 12

Conversion of 4R, S-IHOG to 2R-monatin Using S243N/A182S Mutated BMDAT (1) Preparation of Microbial Cells The *E. coli* transformant containing pS243N/A182S was inoculated to 3 mL of the LB medium (1 g/dL of bacto tryptone, 0.5 g/dL of yeast extract and 1 g/dL of NaCl) containing 0.1 mg/mL of ampicillin, and cultivated at 37° C. for 16 hours. Subsequently, 2.5 mL of thus obtained broth was added to a 500 mL Sakaguchi flask which contains 50 mL of casamino acid medium (0.5 g/dL of ammonium sulfate, 0.14 g/dL of $KH_2PO_4$, 0.23 g/dL of citrate $2Na \cdot 3H_2O$, 0.1 g/dL of $MgSO_4 \cdot 7H_2O$, 2 mg/dL of $FeSO_4$, 2 mg/dL of $MnSO_4$, 2 mg/dL of pyridoxine hydrochloride, 0.1 mg/dL of thiamine, 1 g/dL of casamino acid, 0.3 g/dL of glycerol, pH 7.5) containing 0.1 mg/mL of ampicillin and 0.1 mM IPTG, and then cultured with shaking at 37° C. for 18 hours. Cells were harvested from the cultured medium, and washed to prepare S243N/A182S mutated BMDAT-expressing *E. coli*.

(2) IHOG Amination Reaction

The microbial cells harvested from 240 mL of the cultured medium and washed in the above (1) were suspended in 120 mL of a reaction liquid composed of 100 mM potassium phosphate buffer (pH 8.3), 244 mM 4R, S-IHOG, 600 mM DL-alanine, and 1 mM pyridoxal-5'-phosphate, and stirred at 37° C. for 24 hours. In order to prevent pH reduction during the reaction, pH was controlled to pH 8.4±0.1 with 1 N KOH. As a result, 79.2 mM of (2R, 4R)-monatin was accumulated in the reaction liquid in 24 hours (molar yield per 4R-IHOG is 65%). The obtained reaction liquid was centrifuged at 5,000 rpm for 10 min to obtain a supernatant.

(3) Purification of (2R, 4R)-monatin From Enzymatic Reaction Liquid 121.84 g of the enzyme reaction liquid (containing 2.72 wt % of (2R, 4R)-monatin) was passed through a resin column (diameter: 4 cm) packed with 600 mL of synthetic absorbent (Diaion-SP207 supplied from Mitsubishi Chemical Corporation). Purified water was then passed therethrough at a flow rate of 7.5 /min for 3 hours. An aqueous solution of 15% 2-propanol was then passed therethrough at a flow rate of 7.5 /min for 3 hours. By collecting 2.6 to 3.5 (eluted liquid amount/resin dose (L/L-R)), (2R, 4R)-monatin was almost totally fractionated.

The treated liquid thus obtained was concentrated up to 13.3 g. 64 mL of 2-propanol was added to the concentrated liquid. The mixed solution was stirred at 10° C. for 16 hours. The appeared crystals were filtered off, and 3.0 g of the wet crystal thus obtained was dissolved in 10 mL of water. 30 mL of 2-propanol was added thereto at 35° C., and further 30 mL of 2-propanol was added dropwise over 2 hours at 35° C. The resulting solution was cooled to room temperature. The appeared crystal was filtrated off and dried under the reduced pressure to yield 2.59 g of (2R, 4R)-monatin potassium salt (area purity: 97.4%).

Reference Example 1

Synthesis of IHOG 18.91 g (286.5 mmol, content 85% by weight) of potassium hydroxide was dissolved in 64.45 mL of water. To this solution, 7.50 g (35.8 mmol, content 97.0% by weight) of indole-3-pyruvate and 14.18 g (107.4 mmol) of oxaloacetic acid were added and dissolved therein. This mixed solution was stirred at 35° C. for 24 hours.

Further, 40.0 mL of 3N hydrochloric acid was added thereto for neutralization (pH=7.0), to obtain 153.5 g of the reacted neutralized solution. In this reacted neutralized solution, 5.55 g of IHOG was contained, and the yield (per indole-3-pyruvate) was 53.3%.

Water was added to this reacted neutralized solution to add up the volume thereof to 168 mL. After that, the mixture was then passed through a resin column (diameter 4.8 cm) packed with 840 mL of synthetic absorbent (Diaion-SP207 supplied from Mitsubishi Chemical Corporation). Purified water was then passed therethrough at a flow rate of 23.5 mL per minute and fraction at 1.73 to 2.55 (L/L-R) was collected, whereby an aqueous solution containing 3.04 g of IHOG with high purity was obtained at a yield of 54.7% (per amount of the crude product applied to the resin).

(NMR measurement)

$^1$H-NMR(400 MHz, D$_2$O): 3.03 (d, 1H. J=14.6 Hz), 3.11 (d, 1H, J=14.6 Hz), 3.21(d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz).

$^{13}$C-NMR(100 MHz, D$_2$O): 35.43, 47.91, 77.28, 109.49, 112.05, 119.44, 119.67, 121.91, 125.42, 128.41, 136.21, 169.78, 181.43, 203.58

Reference Example 2

Synthesis of PHOG 13.8 g of potassium hydroxide (purity: 85%) was dissolved in 25 mL of water. To this solution, 5.0 g (30.5 mmol) of phenyl pyruvate and 12.1 g (91.4 mmol) of oxaloacetic acid were added, and the mixture was reacted at room temperature for 72 hours. Using concentrated hydrochloric acid, a pH value of the reaction liquid was adjusted to 2.2, and extraction with ethyl acetate was then performed. An organic layer was washed with saturated brine, dried on magnesium sulfate anhydrate, and concentrated to yield a residue mass. The residue was recrystallized from ethyl acetate and toluene to yield 2.8 g (11.3 mmol) of PHOG as crystals.

(NMR measurement)

$^1$H-NMR (D$_2$O) δ: 2.48 (d, J=14.4 Hz, 0.18H), 2.60(d, J=14.4 Hz, 0.18H), 2.85-3.30 (m, 3.64H), 7.17-7.36 (m, 5H)

(Molecular Weight Measurement)

ESI-MS theoretical value $C_{12}H_{12}O_6$=252.23; analyzed value 251.22 (MH$^-$).

INDUSTRIAL APPLICABILITY

According to the present invention, (2R, 4R)-monatin which may be expected as a sweetener and whose sweetness range is the highest among monatin isomers can be efficiently produced by taking advantage of an enzymatic reaction, and therefore, the present invention is extremely useful industrially, particularly in the field of foods.

What is claimed is:

1. An isolated DNA comprising a nucleotide sequence selected from the group consisting of:

(A) the nucleotide sequence of SEQ ID NO:1, wherein said DNA encodes a protein having a D-aminotransferase activity;

(B) a nucleotide sequence encoding a protein having D-aminotransferase activity which hybridizes under stringent conditions with another DNA composed of a nucleotide sequence complementary to the nucleotide sequence of SEQ ID NO:1, wherein said stringent conditions comprise 65° C., 0.1×SSC and 0.1% SDS;

(C) a nucleotide sequence encoding a protein having the amino acid sequence of SEQ ID NO:2, wherein said protein has a D-aminotransferase activity; and (D) a nucleotide sequence encoding a protein having an amino acid sequence having substitution, deletion, insertion, and/or addition of one to ten amino acid residues in the amino acid sequence SEQ ID NO:2, wherein said protein has a D-aminotransferase activity.

2. An isolated DNA encoding a protein having an amino acid sequence selected from the following (A) and (B):

(A) an amino acid sequence having substitution of an amino acid residue at a position selected from positions 100, 180 to 183, 243 and 244, or combinations thereof, in the amino acid sequence of SEQ ID NO:2; and (B) an amino acid sequence having substitution, deletion, insertion, and/or addition of one or several amino acid residues at position(s) other than positions 100, 180 to 183, 243 and 244 in the amino acid sequence (A), such that a total of one to ten amino acid residues of the amino acid sequence of SEQ ID NO:2 have been altered;
wherein said protein has a D-aminotransferase activity, and wherein an amount of (2R, 4R)-monatin produced with said protein from 4-(indol-3-ylmethyl)-4-hydroxy-2-oxoglutaric acid is greater than that produced with a protein having the amino acid sequence of SEQ ID NO:2.

3. A recombinant DNA obtained by ligating the DNA according to claim 2 to a vector DNA.

4. An isolated cell transformed with the recombinant DNA according to claim 3.

5. A method for producing a protein having a D-aminotransferase activity, comprising culturing the cell according to claim 4 in a medium and accumulating said protein having said D-aminotransferase activity in said medium and/or said cell.

6. The isolated DNA according to claim 1, wherein said DNA has the nucleotide sequence of SEQ ID NO:1.

7. A recombinant DNA obtained by ligating the DNA according to claim 6 to a vector DNA.

8. An isolated cell transformed with the recombinant DNA according to claim 7.

9. A method for producing a protein having a D-aminotransferase activity, comprising culturing the cell according to claim 8 in a medium and accumulating said protein having said D-aminotransferase activity in said medium and/or said cell.

10. The isolated DNA according to claim 1, wherein said DNA encodes a protein having D-aminotransferase and has a nucleotide sequence which hybridizes under stringent conditions with another DNA composed of a nucleotide sequence complementary to the nucleotide sequence of SEQ ID NO:1, wherein said stringent conditions comprise 65° C., 0.1×SSC and 0.1% SDS.

11. A recombinant DNA obtained by ligating the DNA according to claim 10 to a vector DNA.

12. An isolated cell transformed with the recombinant DNA according to claim 11.

13. A method for producing a protein having a D-aminotransferase activity, comprising culturing the cell according to claim 12 in a medium and accumulating said protein having said D-aminotransferase activity in said medium and/or said cell.

14. The isolated DNA according to claim 1, wherein said DNA has a nucleotide sequence encoding a protein having the amino acid sequence of SEQ ID NO:2.

15. A recombinant DNA obtained by ligating the DNA according to claim 14 to a vector DNA.

16. An isolated cell transformed with the recombinant DNA according to claim 15.

17. A method for producing a protein having a D-aminotransferase activity, comprising culturing the cell according to claim 16 in a medium and accumulating said protein having said D-aminotransferase activity in said medium and/or said cell.

18. The isolated DNA according to claim 1, wherein said DNA has a nucleotide sequence encoding a protein having an amino acid sequence having substitution, deletion, insertion, and/or addition of one to ten amino acid residues in the amino acid sequence of SEQ ID NO:2, wherein said protein has a D-aminotransferase activity.

19. A recombinant DNA obtained by ligating the DNA according to claim 18 to a vector DNA.

20. A cell transformed with the recombinant DNA according to claim 19.

21. A method for producing a protein having a D-aminotransferase activity, comprising culturing the cell according to claim 20 in a medium and accumulating said protein having said D-aminotransferase activity in said medium and/or said cell.

22. A method for producing an optically active glutamic acid derivative, comprising:
(a) expressing a recombinant DNA comprising the DNA of claim 1 in a cell containing said recombinant DNA to produce said protein having a D-aminotransferase activity;
(b) reacting a keto acid represented by the following general formula (1):

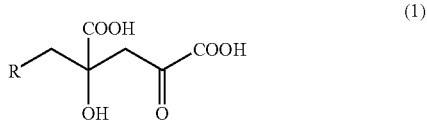

in the presence of said protein and an amino donor, to generate a (2R, 4R) isomer of said glutamic acid derivative represented by the following general formula (2):

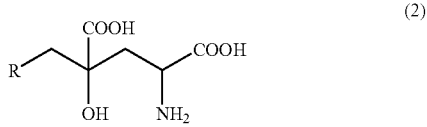

or a salt thereof;
wherein R in the formulae (1) and (2) is an aromatic or heterocyclic ring, and said aromatic or heterocyclic ring may further have one or more of a halogen atom, a hydroxyl group, an alkyl group having up to 3 carbon atoms, an alkoxy group having up to 3 carbon atoms, and an amino group.

23. The method for producing the optically active glutamic acid derivative according to claim 22, wherein said R is a phenyl or indolyl group.

24. The method for producing the optically active glutamic acid derivative according to claim 22, wherein said amino donor is an amino acid.

25. The method for producing the optically active glutamic acid derivative according to claim 24, wherein said reaction is performed in a reaction system further containing an enzyme having an activity to catalyze a reaction for converting an L-amino acid to a D-amino acid, or a microorganism having such an enzymatic activity.

26. The method for producing the optically active glutamic acid derivative according to claim 22, further comprising purifying said protein prior to said reacting.

27. The method for producing the optically active glutamic acid derivative according to claim 22, further comprising isolating said optically active glutamic acid derivative.

28. The isolated DNA according to claim 2, wherein said DNA has a nucleotide sequence encoding a protein having an amino acid sequence selected from (A) or (B):
(A) an amino acid sequence having substitution selected from the group consisting of the following substitutions (a) to (e), or a combination thereof, in an amino acid sequence of SEQ ID NO: 2:
(a) substitution of a serine residue at position 181 with another amino acid residue;

(b) substitution of an alanine residue at position 182 with another amino acid residue;
(c) substitution of an asparagine residue at position 183 with another amino acid residue;
(d) substitution of a serine residue at position 243 with another amino acid residue; and
(e) substitution of a serine residue at position 244 with another amino acid residue; and (B) an amino acid sequence having substitution, deletion, insertion, and/or addition of one or several amino acid residues at position(s) other than positions 181 to 183, 243, and 244 in the amino acid sequence (A), such that a total of one to ten amino acid residues of the amino acid sequence represented by SEQ ID NO: 2 have been altered.

29. The isolated DNA according to claim 28, wherein said group consisting of said substitutions (a) to (e) is the group consisting of the following substitutions (a) to (e):
(a) substitution of the serine residue at position 181 with an aspartic acid residue;
(b) substitution of the alanine residue at position 182 with a lysine or serine residue;
(c) substitution of the asparagine residue at position 183 with a serine residue;
(d) substitution of the serine residue at position 243 with a glutamic acid, leucine, lysine, asparagine or glutamine residue; and
(e) substitution of a serine residue at position 244 with a lysine residue.

30. The isolated DNA according to claim 2, wherein said DNA has a nucleotide sequence encoding a protein having an amino acid sequence selected from (A) or (B):

(A) an amino acid sequence having substitution selected from the group consisting of the following substitutions (a) to (e), or a combination thereof, in the amino acid sequence of SEQ ID NO: 2:
(a) substitution of an asparagine residue at position 100 with another amino acid residue;
(b) substitution of a serine residue at position 181 with another amino acid residue; and
(c) substitution of an alanine residue at position 182 with another amino acid residue; and (B) an amino acid sequence having substitution, deletion, insertion, and/or addition of one or several amino acid residues at position(s) other than positions 100, 181, and 182 in the amino acid sequence (A), such that a total of one to ten amino acid residues of the amino acid sequence represented by SEQ ID NO: 2 have been altered.

31. The isolated DNA according to claim 30, wherein said group consisting of said substitutions (a) to (c) is the group consisting of the following substitutions (a) to (c):
(a) substitution of the asparagine residue at position 100 with an alanine residue;
(b) substitution of the serine residue at position 181 with an alanine residue; and
(c) substitution of the alanine residue at position 182 with a serine residue.

32. The isolated DNA according to claim 2, wherein said DNA has a nucleotide sequence encoding a protein comprising an amino acid sequence having substitution selected from the group consisting of the following substitutions (i) to (vii), or a combination thereof, in the amino acid sequence of SEQ ID NO: 2:
(i) substitution of a serine residue at position 243 with an asparagine residue;
(ii) substitution of a serine residue at position 244 with a lysine residue;
(iii) substitution of a serine residue at position 180 with an alanine residue and substitution of a serine residue at position 243 with an asparagine residue;
(iv) substitution of a serine residue at position 180 with an alanine residue and substitution of a serine residue at position 244 with a lysine residue;
(v) substitution of a serine residue at position 243 with an asparagine residue and substitution of a serine residue at position 244 with a lysine residue;
(vi) substitution of an asparagine residue at position 100 with an alanine residue and substitution of a serine residue at position 243 with an asparagine residue; and
(vii) substitution of an alanine residue at position 182 with a serine residue and substitution of a serine residue at position 243 with an asparagine residue.

33. A method for producing an optically active glutamic acid derivative, comprising:
(a) expressing a recombinant DNA comprising the DNA of claim 2 in a cell containing said recombinant DNA to produce said protein having a D-aminotransferase activity;
(b) reacting a keto acid represented by the following formula (1):

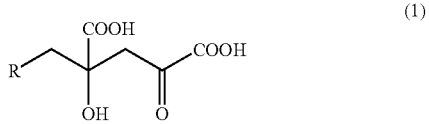

in the presence of the protein and an amino donor, to generate a (2R, 4R) isomer of said glutamic acid derivative represented by the following formula (2):

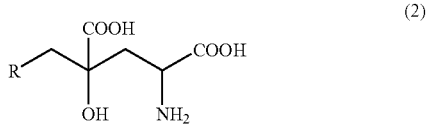

or a salt thereof;
wherein R in the formulae (1) and (2) is an aromatic or heterocyclic ring, and said aromatic or heterocyclic ring may further have one or more of a halogen atom, a hydroxyl group, an alkyl group having up to 3 carbon atoms, an alkoxy group having up to 3 carbon atoms, and an amino group.

34. The method according to claim 33, wherein said R is a phenyl or indolyl group.

35. The method according to claim 33, wherein said amino donor is an amino acid.

36. The method according to claim 35, wherein said reaction is performed in a reaction system further containing an enzyme having an activity to catalyze a reaction for converting an L-amino acid to a D-amino acid, or a microorganism having such an enzymatic activity.

37. The method according to claim 33, further comprising purifying said protein prior to said reacting.

38. The method according to claim 33, further comprising isolating said optically active glutamic acid derivative.

* * * * *

UNITED STATES PATENT AND TRADEMARK OFFICE
CERTIFICATE OF CORRECTION

PATENT NO. : 7,402,412 B2 Page 1 of 1
APPLICATION NO. : 11/148410
DATED : July 22, 2008
INVENTOR(S) : Masakazu Sugiyama et al.

It is certified that error appears in the above-identified patent and that said Letters Patent is hereby corrected as shown below:

In column 5, line 13, "asparagine" should read -- aspartic acid --.

In column 10, line 63, "asparagine" should read -- aspartic acid --.

In column 18, line 15, "asparagine" should read -- aspartic acid --.

Signed and Sealed this

Twenty-seventh Day of April, 2010

David J. Kappos
*Director of the United States Patent and Trademark Office*

SEQUENCE LISTING

```
<160> NUMBER OF SEQ ID NOS: 42

<210> SEQ ID NO 1
<211> LENGTH: 1709
<212> TYPE: DNA
<213> ORGANISM: Bacillus macerans
<220> FEATURE:
<221> NAME/KEY: CDS
<222> LOCATION: (630)..(1481)

<400> SEQUENCE: 1
tacatcaggt agcgccatgc atgacagaaa gggatcatga gcgttatctg ctgcgtttac      60
aacagagtga cgactgagtc agagcaattg tcgactttat cgcagaggtt tttatcagga     120
tcattatgcc atcagcttga gttgcaattc gaggatgcca tgtctggtca gacaacatta     180
aatccaggca ttgttagcta tgatgtcagt aaaggtggca gtttagtgat tagtatgcgc     240
tattctgtgt cctatccatt cgatgaaaaa ttacggaggc tcaacgttta gttgtaaaaa     300
gaggattttc attagatatt caagacgact ccaagcccca ttatgtcagt gaagatgatc     360
catttatcca aacattagcg gctatttata gacgtcaatc aggagataca gaaacaccgt     420
tattatctac aggtggtgga acgtatgcac gtgtgctgaa aaaaggcgtg gcctttggca     480
tgctattccc tggggagcag gatgtggcgc atcgggcgga tgagtttgta gtgattgaaa     540
```

```
atcttgtaaa agcagcggct atttatgcgg aagcaattgt tgagcttgcg ggaaaaaaat        600
aacataaaga cgaaaaggat gaacggaaa atg gca tat tca tta tgg aat gat         653
                                 Met Ala Tyr Ser Leu Trp Asn Asp
                                  1               5 caa att gtt gaa gaa gga tct att gca atc tca cca gaa gac aga ggt         701
Gln Ile Val Glu Glu Gly Ser Ile Ala Ile Ser Pro Glu Asp Arg Gly
    10              15                  20 tat cag ttt ggt gac ggt att tat gaa gta att aaa gtt tat aac gga         749
Tyr Gln Phe Gly Asp Gly Ile Tyr Glu Val Ile Lys Val Tyr Asn Gly
 25              30                  35                  40 aat atg ttt aca gca caa gag cac att gat cgt ttc tat gcg agc gcc         797
Asn Met Phe Thr Ala Gln Glu His Ile Asp Arg Phe Tyr Ala Ser Ala
                 45                  50                  55 gaa aaa att cgc ctt gtt atc cct tat aca aaa gat gtt tta cac aag         845
Glu Lys Ile Arg Leu Val Ile Pro Tyr Thr Lys Asp Val Leu His Lys
             60                  65                  70 tta cta cat gag cta att gaa aag aat aat cta gaa aca gga cat gtt         893
Leu Leu His Glu Leu Ile Glu Lys Asn Asn Leu Glu Thr Gly His Val
         75                  80                  85 tat ttt caa atc act cgt ggg gct aat tca cgt aat cac gtt ttc ccg         941
Tyr Phe Gln Ile Thr Arg Gly Ala Asn Ser Arg Asn His Val Phe Pro
 90              95                 100 gat gca agt att cct gct gta tta act gga aat gta aaa gcg ggt gaa         989
Asp Ala Ser Ile Pro Ala Val Leu Thr Gly Asn Val Lys Ala Gly Glu
105             110                 115                 120 cgt gca tat gaa aac ttt gaa aaa ggt gtt aaa gcc act ttt gtt gag        1037
Arg Ala Tyr Glu Asn Phe Glu Lys Gly Val Lys Ala Thr Phe Val Glu
                125                 130                 135 gat att cgt tgg ttg cgt tgt gac att aaa tct tta aac ttg ctt ggt        1085
Asp Ile Arg Trp Leu Arg Cys Asp Ile Lys Ser Leu Asn Leu Leu Gly
            140                 145                 150 gca gta tta gca aaa caa gaa gct gcg gag aaa ggt tgt tat gaa gcg        1133
Ala Val Leu Ala Lys Gln Glu Ala Ala Glu Lys Gly Cys Tyr Glu Ala
        155                 160                 165 atc tta cat cgc gga gat atc gtg aca gaa tgc tct tca gct aat gtt        1181
Ile Leu His Arg Gly Asp Ile Val Thr Glu Cys Ser Ser Ala Asn Val
    170                 175                 180 tac gga att aaa gat gga aaa ctt tat aca cat cca gct aat aat ttc        1229
Tyr Gly Ile Lys Asp Gly Lys Leu Tyr Thr His Pro Ala Asn Asn Phe
185             190                 195                 200 atc tta aat ggt att aca cgt caa gtc att tta aaa tgt gcg gaa gaa        1277
Ile Leu Asn Gly Ile Thr Arg Gln Val Ile Leu Lys Cys Ala Glu Glu
                205                 210                 215 att aat tta cca gta atc gaa gag cca atg acg aaa gct gat tta cta        1325
Ile Asn Leu Pro Val Ile Glu Glu Pro Met Thr Lys Ala Asp Leu Leu
            220                 225                 230 aca atg gat gaa atc att gtg tcg tct gta tct tct gag gtt acg cca        1373
Thr Met Asp Glu Ile Ile Val Ser Ser Val Ser Ser Glu Val Thr Pro
        235                 240                 245 gtc att gat gtg gac ggc aac caa att ggg gct gga gtt ccc ggt gaa        1421
Val Ile Asp Val Asp Gly Asn Gln Ile Gly Ala Gly Val Pro Gly Glu
    250                 255                 260 tgg act cgt caa tta cag caa tca ttt gaa gcg aaa tta cca ctt tca        1469
Trp Thr Arg Gln Leu Gln Gln Ser Phe Glu Ala Lys Leu Pro Leu Ser
265                 270                 275                 280 atg aat acc aaa taaagaacc ttgtagagaa ctatctgtat ggatagttct             1521
Met Asn Thr Lys ctttatttat gggtgtaatg ttgggtctcg tcatgtaaaa taaaaaggat agtagaataa      1581
```

```
tcttacagat tgaaatttgt agagcaatgt cgatgtaatg aatacataag aatgcataga    1641 ctcttttac aaaggggatc gagaaaaaag agaactaaag agatggtaag taagaatgga    1701
gtgacctt                                                              1709
```

<210> SEQ ID NO 2
<211> LENGTH: 284
<212> TYPE: PRT
<213> ORGANISM: Bacillus macerans

<400> SEQUENCE: 2

```
Met Ala Tyr Ser Leu Trp Asn Asp Gln Ile Val Glu Glu Gly Ser Ile
1               5                   10                  15

Ala Ile Ser Pro Glu Asp Arg Gly Tyr Gln Phe Gly Asp Gly Ile Tyr
            20                  25                  30

Glu Val Ile Lys Val Tyr Asn Gly Asn Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Glu Leu Ile Glu Lys
65                  70                  75                  80

Asn Asn Leu Glu Thr Gly His Val Tyr Phe Gln Ile Thr Arg Gly Ala
                85                  90                  95

Asn Ser Arg Asn His Val Phe Pro Asp Ala Ser Ile Pro Ala Val Leu
            100                 105                 110

Thr Gly Asn Val Lys Ala Gly Glu Arg Ala Tyr Glu Asn Phe Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

Ala Glu Lys Gly Cys Tyr Glu Ala Ile Leu His Arg Gly Asp Ile Val
                165                 170                 175

Thr Glu Cys Ser Ser Ala Asn Val Tyr Gly Ile Lys Asp Gly Lys Leu
            180                 185                 190

Tyr Thr His Pro Ala Asn Asn Phe Ile Leu Asn Gly Ile Thr Arg Gln
        195                 200                 205

Val Ile Leu Lys Cys Ala Glu Glu Ile Asn Leu Pro Val Ile Glu Glu
    210                 215                 220

Pro Met Thr Lys Ala Asp Leu Leu Thr Met Asp Glu Ile Ile Val Ser
225                 230                 235                 240

Ser Val Ser Ser Glu Val Thr Pro Val Ile Asp Val Asp Gly Asn Gln
                245                 250                 255

Ile Gly Ala Gly Val Pro Gly Glu Trp Thr Arg Gln Leu Gln Gln Ser
            260                 265                 270

Phe Glu Ala Lys Leu Pro Leu Ser Met Asn Thr Lys
        275                 280
```

<210> SEQ ID NO 3
<211> LENGTH: 1424
<212> TYPE: DNA
<213> ORGANISM: Bacillus sphaericus
<220> FEATURE:
<221> NAME/KEY: CDS
<222> LOCATION: (427)..(1275)

<400> SEQUENCE: 3

-continued

```
acaaggagga tccgttaatc caaacgttag ctggtgttta tcgccgacaa acgggcgata      60
acgaaacacc tttactttca acaggcggtg gaacgtatgc acgcgtcttg aaaaaaggtg     120
tggcattcgg catgctttc cctggtgatc cagatgtcat gcatcgtgcg gatgaatatg      180
taattgttga taaattagta caagctgctg ctatttatgc agaagccatt gcagaactgg     240
ctgggaagta agtgtcatta agagcgtaat gttttcttgc caaagagatc acgaagcttc     300
acacgccaag cacttcactg aaaaatctac tttgatttac tgcatctggt cttacttgat     360
cgtctagtgg gaatcattgt acttaaaaat gtgaaaataa cttaaaaatg aaaaggatgt     420 ataaac atg gca tac tca tta tgg aat gac caa atc gtt gaa gaa gga       468
       Met Ala Tyr Ser Leu Trp Asn Asp Gln Ile Val Glu Glu Gly
         1               5                  10 tct att aca att tca cca gaa gac cgt ggt tat caa ttt ggt gat ggt      516
Ser Ile Thr Ile Ser Pro Glu Asp Arg Gly Tyr Gln Phe Gly Asp Gly
 15              20                  25                  30 att tac gaa gta atc aaa gta tat aac ggg cat atg ttt aca gca caa      564
Ile Tyr Glu Val Ile Lys Val Tyr Asn Gly His Met Phe Thr Ala Gln
             35                  40                  45 gag cac atc gat cgt ttc tat gct agt gcc gaa aaa att cgc ctt gtt      612
Glu His Ile Asp Arg Phe Tyr Ala Ser Ala Glu Lys Ile Arg Leu Val
         50                  55                  60 att cct tat aca aaa gat gta tta cac aaa tta ttg cat gat tta atc      660
Ile Pro Tyr Thr Lys Asp Val Leu His Lys Leu Leu His Asp Leu Ile
     65                  70                  75 gaa aaa aat aat tta aat aca ggt cat gtt tac ttc caa att aca cgt      708
Glu Lys Asn Asn Leu Asn Thr Gly His Val Tyr Phe Gln Ile Thr Arg
 80                  85                  90 gga aca act tct cgt aac cac att ttc ccg gat gca agc gta cca gca      756
Gly Thr Thr Ser Arg Asn His Ile Phe Pro Asp Ala Ser Val Pro Ala
 95                 100                 105                 110 gtg cta aca ggt aat gtt aaa act ggt gaa cgt tca att gaa aat ttc      804
Val Leu Thr Gly Asn Val Lys Thr Gly Glu Arg Ser Ile Glu Asn Phe
             115                 120                 125 gaa aaa ggc gta aaa gcg aca ttg gtt gaa gat gtt cgt tgg tta cgt      852
Glu Lys Gly Val Lys Ala Thr Leu Val Glu Asp Val Arg Trp Leu Arg
         130                 135                 140 tgt gat att aaa tct tta aat tta ctt ggc gcg gta ctt gcg aaa caa      900
Cys Asp Ile Lys Ser Leu Asn Leu Leu Gly Ala Val Leu Ala Lys Gln
     145                 150                 155 gaa gca tct gaa aaa ggt tgt tac gaa gcc att tta cac cgt gga gat      948
Glu Ala Ser Glu Lys Gly Cys Tyr Glu Ala Ile Leu His Arg Gly Asp
160                 165                 170 att atc aca gaa tgt tct tct gct aat gtc tat ggt att aaa gat ggt      996
Ile Ile Thr Glu Cys Ser Ser Ala Asn Val Tyr Gly Ile Lys Asp Gly
175                 180                 185                 190 aaa ctt tat acg cac cca gca aat aac tac atc tta aat ggt att aca     1044
Lys Leu Tyr Thr His Pro Ala Asn Asn Tyr Ile Leu Asn Gly Ile Thr
             195                 200                 205 cgc caa gtt ata tta aaa tgt gcc gct gaa ata aat tta cca gtg att     1092
Arg Gln Val Ile Leu Lys Cys Ala Ala Glu Ile Asn Leu Pro Val Ile
         210                 215                 220 gaa gag ccg atg aca aaa ggc gat tta tta aca atg gat gaa att att     1140
Glu Glu Pro Met Thr Lys Gly Asp Leu Leu Thr Met Asp Glu Ile Ile
     225                 230                 235 gtg tct tct gtt tca tct gaa gtg aca ccg gtt atc gat gtg gat ggt     1188
Val Ser Ser Val Ser Ser Glu Val Thr Pro Val Ile Asp Val Asp Gly
240                 245                 250
```

```
cag caa att ggt gca ggt gtt cct ggt gaa tgg act cgt aaa ttg caa      1236
Gln Gln Ile Gly Ala Gly Val Pro Gly Glu Trp Thr Arg Lys Leu Gln
255                 260                 265                 270 aaa gca ttt gag gca aaa tta cca att tca att aat gcc taatctgtat       1285
Lys Ala Phe Glu Ala Lys Leu Pro Ile Ser Ile Asn Ala
                275                 280 aaatgattaa aaagagctac ctaaaacttg gttattcgcc aagttaggag gtagctctt     1345 ttttatagaa caaatatgc atgtattctc ctgaaacgtc atgtaaaata aaaaagatag     1405
cgcctttagt cgatatcac                                                  1424

<210> SEQ ID NO 4
<211> LENGTH: 283
<212> TYPE: PRT
<213> ORGANISM: Bacillus sphaericus

<400> SEQUENCE: 4
```

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
                20                  25

```
<212> TYPE: DNA
<213> ORGANISM: Artificial Sequence
<220> FEATURE:
<223> OTHER INFORMATION: Synthetic DNA

<400> SEQUENCE: 5
gatatcgtga cagaatgcgc ttcagctaat gtttacgg                              38

<210> SEQ ID NO 6
<211> LENGTH: 38
<212> TYPE: DNA
<213> ORGANISM: Artificial Sequence
<220> FEATURE:
<223> OTHER INFORMATION: Synthetic DNA

<400> SEQUENCE: 6
ccgtaaacat tagctgaagc gcattctgtc acgatatc                              38

<210> SEQ ID NO 7
<211> LENGTH: 38
<212> TYPE: DNA
<213> ORGANISM: Artificial Sequence
<220> FEATURE:
<223> OTHER INFORMATION: Synthetic DNA

<400> SEQUENCE: 7
gatatcgtga cagaatgctc tgacgctaat gtttacgg                              38

<210> SEQ ID NO 8
<211> LENGTH: 38
<212> TYPE: DNA
<213> ORGANISM: Artificial Sequence
<220> FEATURE:
<223> OTHER INFORMATION: Synthetic DNA

<400> SEQUENCE: 8
ccgtaaacat tagcgtcaga gcattctgtc acgatatc                              38

<210> SEQ ID NO 9
<211> LENGTH: 36
<212> TYPE: DNA
<213> ORGANISM: Artificial Sequence
<220> FEATURE:
<223> OTHER INFORMATION: Synthetic DNA

<400> SEQUENCE: 9
cagaatgctc ttcaaagaat gtttacggaa ttaaag                                36

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
ctttaattcc gtaaacattc tttgaagagc attctg                                36

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
```
gtgacagaat gctcttcagc tagtgtttac ggaattaaag                                  40

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
ctttaattcc gtaaacacta gctgaagagc attctgtcac                                  40

<210> SEQ ID NO 13
<211> LENGTH: 36
<212> TYPE: DNA
<213> ORGANISM: Artificial Sequence
<220> FEATURE:
<223> OTHER INFORMATION: Synthetic DNA

<400> SEQUENCE: 13
gaaatcattg tgtcgtctgt agagtctgag gttacg                                      36

<210> SEQ ID NO 14
<211> LENGTH: 36
<212> TYPE: DNA
<213> ORGANISM: Artificial Sequence
<220> FEATURE:
<223> OTHER INFORMATION: Synthetic DNA

<400> SEQUENCE: 14
cgtaacctca gactctacag acgacacaat gatttc                                      36

<210> SEQ ID NO 15
<211> LENGTH: 36
<212> TYPE: DNA
<213> ORGANISM: Artificial Sequence
<220> FEATURE:
<223> OTHER INFORMATION: Synthetic DNA

<400> SEQUENCE: 15
gaaatcattg tgtcgtctgt attgtctgag gttacg                                      36

<210> SEQ ID NO 16
<211> LENGTH: 36
<212> TYPE: DNA
<213> ORGANISM: Artificial Sequence
<220> FEATURE:
<223> OTHER INFORMATION: Synthetic DNA

<400> SEQUENCE: 16
cgtaacctca gacaatacag acgacacaat gatttc                                      36

<210> SEQ ID NO 17
<211> LENGTH: 45
<212> TYPE: DNA
<213> ORGANISM: Artificial Sequence
<220> FEATURE:
<223> OTHER INFORMATION: Synthetic DNA

<400> SEQUENCE: 17
gatgaaatca ttgtgtcgtc tgtaaaatct gaggttacgc cagtc                            45

<210> SEQ ID NO 18
<211> LENGTH: 45
<212> TYPE: DNA
<213> ORGANISM: Artificial Sequence
<220> FEATURE:
<223> OTHER INFORMATION: Synthetic DNA

<400> SEQUENCE: 18
gactggcgta acctcagatt ttacagacga cacaatgatt tcatc        45

<210> SEQ ID NO 19
<211> LENGTH: 40
<212> TYPE: DNA
<213> ORGANISM: Artificial Sequence
<220> FEATURE:
<223> OTHER INFORMATION: Synthetic DNA

<400> SEQUENCE: 19
gaaatcattg tgtcgtctgt aaattctgag gttacgccag        40

<210> SEQ ID NO 20
<211> LENGTH: 40
<212> TYPE: DNA
<213> ORGANISM: Artificial Sequence
<220> FEATURE:
<223> OTHER INFORMATION: Synthetic DNA

<400> SEQUENCE: 20
ctggcgtaac ctcagaattt acagacgaca caatgatttc        40

<210> SEQ ID NO 21
<211> LENGTH: 40
<212> TYPE: DNA
<213> ORGANISM: Artificial Sequence
<220> FEATURE:
<223> OTHER INFORMATION: Synthetic DNA

<400> SEQUENCE: 21
gaaatcattg tgtcgtctgt acagtctgag gttacgccag        40

<210> SEQ ID NO 22
<211> LENGTH: 40
<212> TYPE: DNA
<213> ORGANISM: Artificial Sequence
<220> FEATURE:
<223> OTHER INFORMATION: Synthetic DNA

<400> SEQUENCE: 22
ctggcgtaac ctcagactgt acagacgaca caatgatttc        40

<210> SEQ ID NO 23
<211> LENGTH: 41
<212> TYPE: DNA
<213> ORGANISM: Artificial Sequence
<220> FEATURE:
<223> OTHER INFORMATION: Synthetic DNA

<400> SEQUENCE: 23
cattgtgtcg tctgtatcta aagaggttac gccagtcatt g        41

<210> SEQ ID NO 24
<211> LENGTH: 41
<212> TYPE: DNA
<213> ORGANISM: Artificial Sequence
<220> FEATURE:
<223> OTHER INFORMATION: Synthetic DNA

<400> SEQUENCE: 24
caatgactgg cgtaacctct ttagatacag acgacacaat g        41

<210> SEQ ID NO 25
<211> LENGTH: 40
<212> TYPE: DNA
<213> ORGANISM: Artificial Sequence
<220> FEATURE:
<223> OTHER INFORMATION: Synthetic DNA

<400> SEQUENCE: 25
gaaatcattg tgtcgtctgt aaataaagag gttacgccag                40

<210> SEQ ID NO 26
<211> LENGTH: 40
<212> TYPE: DNA
<213> ORGANISM: Artificial Sequence
<220> FEATURE:
<223> OTHER INFORMATION: Synthetic DNA

<400> SEQUENCE: 26
ctggcgtaac ctctttattt acagacgaca caatgatttc                40

<210> SEQ ID NO 27
<211> LENGTH: 29
<212> TYPE: DNA
<213> ORGANISM: Artificial Sequence
<220> FEATURE:
<223> OTHER INFORMATION: Synthetic DNA

<400> SEQUENCE: 27
ccgggattcg ttaatccaaa cgttagctg                29

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA

<400> SEQUENCE: 28
ggcctgcagt taggcattaa ttgaaattgg                30

<210> SEQ ID NO 29
<211> LENGTH: 39
<212> TYPE: DNA
<213> ORGANISM: Artificial Sequence
<220> FEATURE:
<223> OTHER INFORMATION: Synthetic DNA

<400> SEQUENCE: 29
gaaattattg tgtcttctgt taaatctgaa gtgacaccg                39

<210> SEQ ID NO 30
<211> LENGTH: 39
<212> TYPE: DNA
<213> ORGANISM: Artificial Sequence
<220> FEATURE:
<223> OTHER INFORMATION: Synthetic DNA

<400> SEQUENCE: 30
cggtgtcact tcagatttaa cagaagacac aataatttc                39

<210> SEQ ID NO 31
<211> LENGTH: 39
<212> TYPE: DNA
<213> ORGANISM: Artificial Sequence
<220> FEATURE:
<223> OTHER INFORMATION: Synthetic DNA

<400> SEQUENCE: 31
gaaattattg tgtcttctgt taactctgaa gtgacaccg        39

<210> SEQ ID NO 32
<211> LENGTH: 39
<212> TYPE: DNA
<213> ORGANISM: Artificial Sequence
<220> FEATURE:
<223> OTHER INFORMATION: Synthetic DNA

<400> SEQUENCE: 32
cggtgtcact tcagagttaa cagaagacac aataatttc        39

<210> SEQ ID NO 33
<211> LENGTH: 36
<212> TYPE: DNA
<213> ORGANISM: Artificial Sequence
<220> FEATURE:
<223> OTHER INFORMATION: Synthetic DNA

<400> SEQUENCE: 33
gtgtcttctg tttcaaaaga agtgacaccg gttatc           36

<210> SEQ ID NO 34
<211> LENGTH: 36
<212> TYPE: DNA
<213> ORGANISM: Artificial Sequence
<220> FEATURE:
<223> OTHER INFORMATION: Synthetic DNA

<400> SEQUENCE: 34
gataaccggt gtcacttctt ttgaaacaga agacac           36

<210> SEQ ID NO 35
<211> LENGTH: 35
<212> TYPE: DNA
<213> ORGANISM: Artificial Sequence
<220> FEATURE:
<223> OTHER INFORMATION: Synthetic DNA

<400> SEQUENCE: 35
ggggctaatt cacgtgctca cgttttcccg gatgc            35

<210> SEQ ID NO 36
<211> LENGTH: 35
<212> TYPE: DNA
<213> ORGANISM: Artificial Sequence
<220> FEATURE:
<223> OTHER INFORMATION: Synthetic DNA

<400> SEQUENCE: 36
gcatccggga aaacgtgagc acgtgaatta gcccc            35

<210> SEQ ID NO 37
<211> LENGTH: 32
<212> TYPE: DNA
<213> ORGANISM: Artificial Sequence
<220> FEATURE:
<223> OTHER INFORMATION: Synthetic DNA

<400> SEQUENCE: 37
gtgacagaat gctctgcagc taatgtttac gg               32

<210> SEQ ID NO 38

```
<211> LENGTH: 32
<212> TYPE: DNA
<213> ORGANISM: Artificial Sequence
<220> FEATURE:
<223> OTHER INFORMATION: Synthetic DNA

<400> SEQUENCE: 38
ccgtaaacat tagctgcaga gcattctgtc ac                                    32

<210> SEQ ID NO 39
<211> LENGTH: 40
<212> TYPE: DNA
<213> ORGANISM: Artificial Sequence
<220> FEATURE:
<223> OTHER INFORMATION: Synthetic DNA

<400> SEQUENCE: 39
gtgacagaat gctcttcatc taatgtttac ggaattaaag                            40

<210> SEQ ID NO 40
<211> LENGTH: 40
<212> TYPE: DNA
<213> ORGANISM: Artificial Sequence
<220> FEATURE:
<223> OTHER INFORMATION: Synthetic DNA

<400> SEQUENCE: 40
ctttaattcc gtaaacatta gatgaagagc attctgtcac                            40

<210> SEQ ID NO 41
<211> LENGTH: 38
<212> TYPE: DNA
<213> ORGANISM: Artificial Sequence
<220> FEATURE:
<223> OTHER INFORMATION: Synthetic DNA

<400> SEQUENCE: 41
gatatcgtga cagaatgctc tgcatctaat gtttacgg                              38

<210> SEQ ID NO 42
<211> LENGTH: 38
<212> TYPE: DNA
<213> ORGANISM: Artificial Sequence
<220> FEATURE:
<223> OTHER INFORMATION: Synthetic DNA

<400> SEQUENCE: 42
ccgtaaacat tagatgcaga gcattctgtc acgatatc                              38
```